United States Patent [19]

Takemoto et al.

[11] Patent Number: 5,262,415
[45] Date of Patent: Nov. 16, 1993

[54] AMINOPYRIDINE COMPOUNDS

[75] Inventors: Tadahiro Takemoto; Masahiro Eda; Mitsuyoshi Hihara; Takehiro Okada; Hiroshi Sakashita; Miyuki Eiraku; Chikara Fukaya; Norifumi Nakamura; Masanori Sugiura; Sumio Matzno; Maki Goda, all of Osaka; Yasumi Uchida, Chiba, all of Japan

[73] Assignee: The Green Cross Corporation, Osaka, Japan

[21] Appl. No.: 850,817

[22] Filed: Mar. 13, 1992

[30] Foreign Application Priority Data

Mar. 15, 1991 [JP] Japan .................. 3-76777

[51] Int. Cl.$^5$ .................. A61K 31/495; A61K 31/54; A61K 31/44; C07D 401/00; C07D 211/56; C07D 211/72
[52] U.S. Cl. .................. 514/252; 514/227.8; 514/235.8; 514/336; 514/340; 514/341; 514/344; 514/346; 544/60; 544/124; 544/360; 546/193; 546/215; 546/275; 546/276; 546/278; 546/279; 546/281; 546/287; 546/289; 546/297; 546/305; 546/306
[58] Field of Search .................. 544/60, 124, 360; 546/278, 279, 287, 289, 297, 305, 306, 193, 215, 275, 276, 281; 514/227.8, 235.8, 252, 341, 344, 346, 318, 336, 340

[56] References Cited

U.S. PATENT DOCUMENTS

| 4,057,636 | 11/1977 | Petersen | 546/306 |
| 4,436,911 | 3/1984 | Studt et al. | 546/306 |
| 4,496,573 | 1/1985 | Studt et al. | 546/306 |
| 4,787,931 | 11/1988 | Henrie II, et al. | 546/306 |
| 4,808,722 | 2/1989 | Henrie II | 546/306 |
| 4,818,271 | 4/1989 | Henrie II | 546/306 |

FOREIGN PATENT DOCUMENTS

| 0006628 | 1/1980 | European Pat. Off. . |
| 0055179 | 6/1982 | European Pat. Off. . |
| 0354553 | 2/1990 | European Pat. Off. . |
| 381504 | 8/1990 | European Pat. Off. ......... 546/306 |
| 0392802 | 10/1990 | European Pat. Off. . |
| 2557438 | 6/1976 | Fed. Rep. of Germany ...... 546/306 |
| 2143702 | 2/1973 | France . |
| 2105331 | 3/1983 | United Kingdom .............. 546/306 |

OTHER PUBLICATIONS

Novikov et al. CA 70-777272 (1967 Computer Print Out is Provided for CA and Structure.

Primary Examiner—Cecilia Tsang
Attorney, Agent, or Firm—Sughrue, Mion, Zinn, Macpeak & Seas

[57] ABSTRACT

An aminopyridine compound represented by the formula:

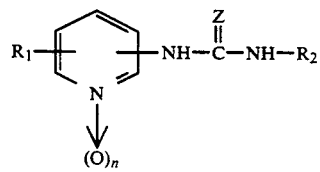

wherein n represents 0 or 1; Z represents =S, =O, =NCN or =CHNO$_2$; R$_1$ represents —CN, —NR$_3$R$_4$, —CONR$_3$R$_4$, —NHNR$_3$R$_4$, —NHCONHR$_3$, —NHSO$_2$R$_3$ or —SR$_3$; R$_2$ represents H, or substituted or unsubstituted alkyl; R$_3$ and R$_4$, which may be the same or different, represent H, substituted or unsubstituted alkyl, aryl, substituted or unsubstituted acyl or alkoxycarbonyl group; and R$_3$ and R$_4$ may form a heterocyclic ring together with a nitrogen atom to which R$_3$ and R$_4$ are bound, through another heteroatom or without it; or an acid salt thereof, which is excellent in pharmacological effect and repressed in side effects as a drug for circulatory diseases.

20 Claims, No Drawings

AMINOPYRIDINE COMPOUNDS

FIELD OF THE INVENTION

The present invention relates to novel aminopyridine compounds useful as agents for treating diseases of the circulatory system.

BACKGROUND OF THE INVENTION

As agents for the circulatory system, particularly therapeutic agents for hypertension, various compounds are commercially available or currently under development. In recent years, the possibility of treatment of circulatory diseases based on a new mechanism called "potassium channel opener" has been suggested and various investigations have been made, based on this theory.

Typical examples of drugs based on the above mechanism are Pinacidil [N''-cyano-N-4-pyridyl-N'-(1,2,2-trimethylpropyl)guanidine] having an N-pyridyl-N'-cyanoguanidine skeleton and Cromakalim [(+,−)-6-cyano-3,4-dihydro -2,2-dimethyl-trans-4-(2-oxo-1-pyrrolidinyl))-2H -benzo(b)pyran-3-ol] having a benzopyran skeleton.

At present, however, it cannot be said that Pinacidil nor Cromakalim possess sufficient pharmacological effects without side effects. In particular, Pinacidil causes stagnation as a side effect, and the problems of edema, vascular headache, cardiopalmus, etc. remain unsolved.

In order to solve the above problems, new compounds thought to have an improved overall pharmacological effect are currently under investigation.

As such compounds, N-alkyl-N'-pyridyl-thioureas and N-alkyl-N'-pyridyl-N'-cyanoguanidines [JP-A-51-86474 (the term "JP-A" as used herein means an "unexamined published Japanese patent application") and JP-A-52-83573 corresponding to U.S. Pat. No. 4,057,636] and N-substituted-N-aryl-thioureas and N-substituted-N-aryl-N'-cyanoguanidines (JP-A-2-91057 corresponding to EP 354553 and JP-A-2-290841 corresponding to EP 392802) have been reported.

SUMMARY OF THE INVENTION

The present inventors conducted intensive investigation in view of the above-described situation. As a result, the present inventors succeeded in synthesizing novel compounds showing excellent pharmacological effect and relieved side effects, compared to Pinacidil which is a known compound, and other compounds having similar structures.

The present invention provides aminopyridine compounds represented by formula (1):

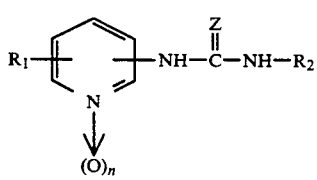

(1)

wherein n represents 0 or 1; Z represents =S, =O, =NCN or =CHNO$_2$; R$_1$ represents —CN, —NR$_3$R$_4$, —CONR$_3$R$_4$, —NHNR$_3$R$_4$, —NHCONHR$_3$, —NH—SO$_2$R$_3$ or —SR$_3$; R$_2$ represents H or substituted or unsubstituted alkyl; R$_3$ and R$_4$, which may be the same or different, represent H, substituted or unsubstituted alkyl, aryl, substituted or unsubstituted acyl or alkoxycarbonyl group; and R$_3$ and R$_4$ may form a heterocyclic ring together with the nitrogen atom to which R$_3$ and R$_4$ are bound, which ring may include another heteroatom and/or contain unsaturation; and the pharmaceutically acceptable acid salts thereof.

DETAILED DESCRIPTION OF THE INVENTION

In the present invention, the alkyl group is preferably a lower alkyl group having 1 to 10 carbon atoms. The alkyl group may be straight or branched chain having 1 to 7 carbon atoms. Specific examples thereof include methyl, ethyl, n-propyl, iso-propyl, n-butyl, iso-butyl, tert-butyl, n-pentyl, n-hexyl, 1,2,2-trimethylpropyl, 2-methylpropyl and 1,1-dimethylpropyl. This type alkyl group may have a substituent group such as a hydroxyl group or an amino group. R$_2$ is preferably a branched alkyl such as 1,2,2-trimethylpropyl, 2-methylpropyl and 1,1-dimethylpropyl.

The alkyl group can be a cycloalkyl group. The cycloalkyl groups include monocycloalkyl, bicycloalkyl, tricycloalkyl and polycycloalkyl groups. Preferably, the cycloalkyl group has 5 to 10 carbon atoms. Specific examples thereof include cyclopentyl, cyclohexyl and cycloheptyl. Examples of the bicycloalkyl groups include norbornyl, pinanyl and bicyclo-[2,2,2]-octyl, and examples of the tricycloalkyl and polycycloalkyl groups include adamantyl. The cycloalkyl group may have a substituent group such as an alkyl group. R$_2$ is preferably bicycloalkyls having 7 to 10 carbon atoms such as bicyclohexyl, norbornyl, pinanyl, bicyclo-[2,2,2]-octyl.

Examples of the aryl groups include phenyl and naphthyl. The aryl group may have a substituent group such as an alkyl group, a halogen atom, a nitro group or a cyano group.

The acyl group may either be an aliphatic acyl group or an aromatic acyl group. When the acyl group is the aliphatic acyl group, an acyl group having 1 to 7 carbon atoms is preferably used. An acyl group having 2 to 5 carbon atoms is more preferred. The acyl group may be straight or branched chain. Specific examples thereof include acetyl, propionyl, butyryl, isobutyryl, valeryl and pivaloyl. The acyl group may have a substituent group such as an amino group, a lower alkoxycarbonylamino group, a carboxy group or a heterocyclic ring. Specific examples thereof include glycyl, alanyl, valyl, prolyl, methionyl, aspartyl, glutamyl, histidyl, N-ethoxycarbonylalanyl, N-t-butoxycarbonylalan-yl. The lower alkoxycarbonyl portion of the lower alkoxycarbonylamino group and the heterocyclic ring include groups described below.

Examples of the aromatic acyl groups include benzoyl, naphthoyl and toluoyl.

The alkoxycarbonyl group whose alkoxy portion is an alkoxy group having 1 to 7 carbon atoms is preferred, and an alkoxy group having 1 to 4 carbon atoms is more preferred. The alkoxy portion may be straight or branched. Specific examples thereof include methoxycarbonyl, ethoxycarbonyl, propoxycarbonyl and butoxycarbonyl. The alkoxy portion may be an aromatic alkoxy group such as benzyloxycarbonyl.

An example of the heterocyclic ring formed by R$_3$, R$_4$ and the nitrogen atom bound thereto is a heterocyclic ring formed with an alkylene group or an alkenylene group constituted by R$_3$ and R$_4$. The alkylene group preferably has 2 to 5 carbon atoms, and may be straight or branched chain. Specific examples thereof include methylene, ethylene, trimethylene, propylene, tetramethylene and 1,2-dimethylethylene. Examples of the alkenylene groups include 1-butenylene and 1,3-butadienylene. Specific examples of these heterocyclic groups include pyrrolidinyl, piperidino, pyrrolinyl and pyrrolyl.

The heterocyclic ring may be formed by $R_3$, $R_4$ and the nitrogen atom to which $R_3$ and $R_4$ are bound, through a second heteroatom (for example, nitrogen, oxygen or sulfur). Examples of these heterocyclic groups include piperazinyl, morpholino, thiomorpholino, imidazolinyl, imidazolidinyl, imidazolyl and pyrazolidinyl. In particular, imidazolyl or a group represented by the following formula:

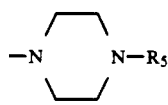

(2)

wherein $R_5$ represents H, alkyl, acyl, aryl or alkoxycarbonyl as above defined; is preferably used. Examples of the alkyl, acyl, aryl and alkoxycarbonyl groups represented by $R_5$ include the groups described above.

It is particularly preferred that substituent group $R_1$ and substituent group —NH—C(=Z)—NHR$_2$ are bound to the pyridine skeleton at the 6-position and 3-position, 2-position and 5-position, 4-position and 3-position or 4-position and 5-position, respectively.

When the aminopyridine compounds of the present invention have asymmetric carbon atoms, optical isomers thereof and the mixture of the optical isomers are included in the scope of the present invention.

The compounds of the present invention can be prepared, for example, by the following methods, although they can be synthesized by other methods apparent to the skilled artisan.

Reaction Process 1

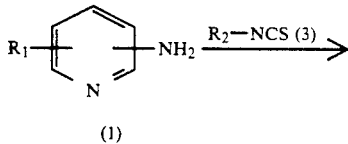

(1)

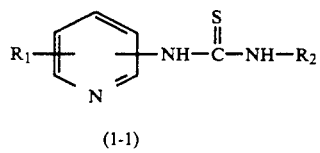

(1-1)

(when n is 0 and Z is S)

wherein $R_1$ and $R_2$ have the same meanings as given above.

The compound represented by formula (1-1) is obtained by reacting the compound represented by formula (2) with the compound represented by formula (3). This reaction is usually conducted in a solvent. As such a solvent, any solvent may be used as long as it does not exert an adverse effect on the reaction. Examples of such solvents include ethers such as diethyl ether, tetrahydrofuran and dioxane; hydrocarbon halides such as dichloromethane, dichloroethane, chloroform and carbon tetrachloride; aromatic hydrocarbons such as benzene, toluene and xylene; amines such as pyridine and piperidine; and aprotic polar solvents such as dimethylformamide (DMF) and dimethyl sulfoxide.

The amount of the compound of formula (3) to the compound represented by formula (2) is about 0.9 to 5 times, and preferably about equimolar to 3 times the molar quantity of the compound represented by formula (2).

This reaction is conducted at about 10° to 80° C., preferably at room temperature (namely, about 15° to 25° C.), for about 1 to 200 hours.

Reaction Process 2

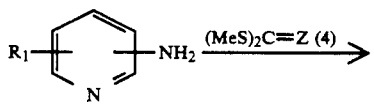

(2)

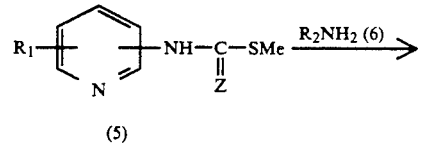

(5)

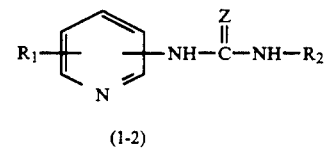

(1-2)

(when n is 0 and Z is NCN or CHNO$_2$)

wherein $R_1$ and $R_2$ have the same meanings as given above.

First Step

In the first step of this reaction process, the compound represented by formula (2) is reacted with the compound represented by formula (4) to obtain the compound represented by formula (5). This reaction is usually conducted in a solvent. As such a solvent, any solvent may be used as long as it has no adverse effect on the reaction. Examples of such solvents include the solvents described above. In particular, the polar solvents such as pyridine, dimethylformamide (DMF) and dimethyl sulfoxide are suitably used.

The amount of the compound of formula (4) used to the compound represented by formula (2) is about 0.9 to 5 times, and preferably about equimolar to twice the molar quantity of the compound represented by formula (2).

This reaction is conducted at about 10 to 80° C, preferably at room temperature (namely, about 15 to 25° C), for about 1 to 200 hours.

Second Step

In the second step, the compound represented by formula (6) is reacted with the compound of formula (5) obtained above to obtain the compound represented by formula (1-2). This reaction may be conducted in a solvent or in a solvent-free state. As such a solvent, any solvent may be used as long as it has no adverse effect on the reaction. For example, polar solvents such as dimethylformamide (DMF) and dimethyl sulfoxide are suitably used.

The amount of the compound of formula (6) used to the compound represented by formula (5) is about 0.9 to 10 times, and preferably about equimolar to 3 times the molar quantity of the compound represented by formula (5).

This reaction is conducted at about 10° to 90° C. for about 1 to 100 hours.

When $R_1$ is not $NH_2$, the raw material compound represented by formula (2) can be prepared by the following method.

Reaction Process 3

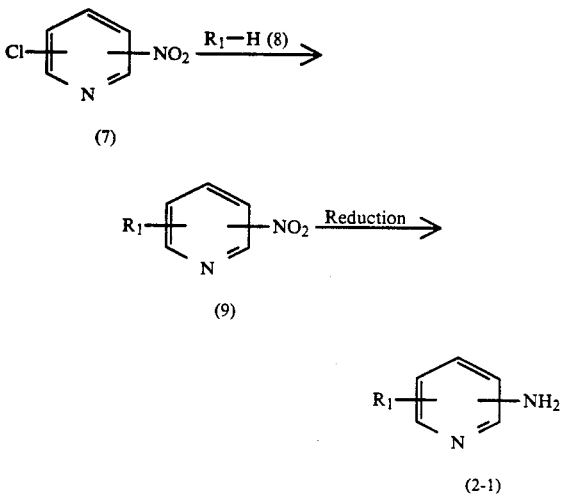

[when n is 0 and $R_1$ is $NR_3R_4$
(with the proviso that $R_1$ is not $NH_2$) or $NHNR_3R_4$]

wherein $R_1$ has the same meaning as given above.

First Step

In the first step of this reaction process, the compound represented by formula (7) is reacted with the compound represented by formula (8) to obtain the compound represented by formula (9). This reaction is usually conducted in a solvent. As such a solvent, any solvent may be used as long as it has no adverse effect on the reaction. Examples of such solvents include the solvents described above. It is preferred that this reaction is conducted in the presence of a basic substance. Examples of such basic substances include triethylamine, tributylamine, 1,5-diazabicyclo[4.3.0]nonene-5 (DBN) and 1,8-diazabicyclo[5.4.0]undecene-7 (DBU).

The amount of the compound of formula (8) used to the compound represented by formula (7) is about 0.9 to 5 times, and preferably about equimolar to 3 times the molar quantity of the compound represented by formula (7). The amount of the basic substance used is about equimolar to 5 times, and preferably about 1.5 to 3 times the molar quantity of the compound represented by formula (7).

This reaction is conducted at about 10° to 100° C. for about 5 minutes to 50 hours.

Second Step

In the second step, the nitro group of the compound of formula (9) obtained above is reduced to obtain the compound represented by formula (2-1). This reaction can be conducted by any method as long as a nitro group is converted into a an amino group, and is usually conducted by catalytic reduction in the presence of a appropriate reduction catalyst. Examples of such reduction catalysts include platinum oxide, palladium black, palladium carbon and Raney nickel. These reduction catalysts are generally used in an amount of about 0.1 to 0.5 times the weight of the compound represented by formula (9).

This catalytic reduction is conducted in a solvent such as ethanol, dioxane, tetrahydrofuran and chloroform, in a hydrogen atmosphere of ordinary pressure to about 5 kg/cm² at about 10° to 40° C., preferably at room temperature (namely, about 15° to 25° C.) for about 1 to 30 hours.

Reaction Process 4

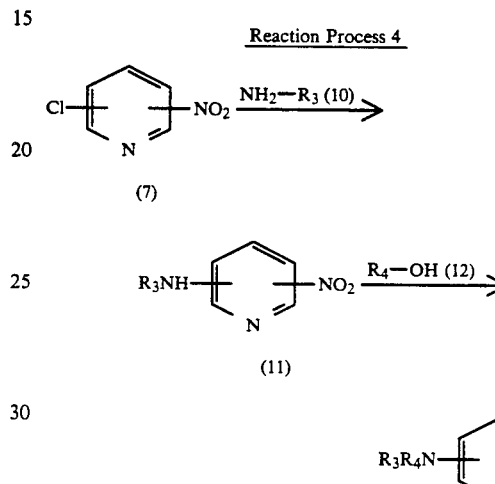

(when n is 0 and $R_1$ is $NR_3R_4$ and $R_4$ is acyl)

wherein $R_3$ and $R_4$ have the same meanings as given above.

First Step

In the first step of this reaction process, the compound represented by formula (7) is reacted with the compound represented by formula (10) to obtain the compound represented by formula (11). This reaction is conducted in a solvent-free state or in a solvent. As such a solvent, any solvent may be used as long as it has no adverse effect on the reaction. Examples of such solvents include the solvents described above. It is preferred that this reaction is conducted using the compound of formula (10) in excess or in the presence of a basic substance. Examples of such basic substances include the substances described above.

The amount of the compound of formula (10) used to the compound represented by formula (7) is about 0.9 to 5 times, and preferably about equimolar to 3 times the molar quantity of the compound represented by formula (7). The amount of the basic substance used is about equimolar to 5 times, and preferably about 1.5 to 3 times the molar quantity of the compound represented by formula (7).

This reaction is conducted at about 50° to 140° C. for about 1 to 50 hours.

Second Step

In the second step, the carboxylic acid compound represented by formula (12) or in which compound the carboxyl group is activated is reacted with the compound of formula (11) obtained above to obtain the compound represented by formula (9-1). This reaction can be conducted in accordance with conventional amide forming reaction methods such as methods using condensing agents (for example, DCC), mixed acid anhydride methods, active esterification methods and methods using carboxylic acid halides. This reaction is usually conducted in a solvent. As such a solvent, any solvent may be used as long as it has no adverse effect on the reaction. Examples of such solvents include the solvents described above. When the methods using carboxylic acid halides are employed, it is preferred that the reaction is conducted in the presence of basic substances. Examples of the basic substances include the above-described basic substances and basic alkaline metal salts.

The amount of the compound of formula (12) used to the compound represented by formula (11) is about 0.9 to 5 times, and preferably about equimolar to twice the molar quantity of the compound represented by formula (11). The amount of the basic substance used is about equimolar to 5 times, and preferably about 1.5 to 3 times the molar quantity of the compound represented by formula (11). This reaction is conducted under ice cooling or at up to about 80° C. for 1 minute to 30 hours.

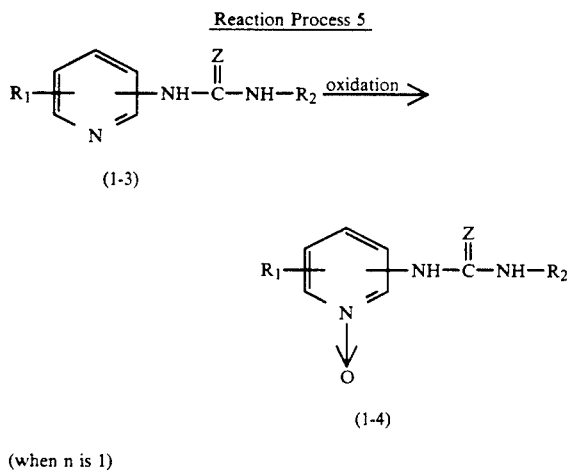

(when n is 1)

wherein $R_1$, $R_2$ and Z have the same meanings as given above

The compound represented by formula (1-4) is obtained by oxidation of the compound represented by formula (1-3) using an oxidant. This reaction is usually conducted in a solvent. Any solvent may be used in this reaction as long as it does not exert an adverse effect on the reaction. Examples of the solvents include hydrocarbon halides such as dichloromethane, dichloroethane, chloroform and carbon tetrachloride; alcohols such as methanol and ethanol; aromatic hydrocarbons such as benzene, toluene and xylene; and fatty acids such as acetic acid and propionic acid. Examples of the oxidant used in this reaction include peracetic acid, perbenzoic acid, m-chloroperbenzoic acid and hydrogen peroxide.

The amount of the oxidant is about 0.9 to 2 times, preferably about equimolar to 1.2 times the molar quantity of the compound represented by formula (1-3).

This reaction is conducted under ice cooling or at up to room temperature for 1 to 10 hours.

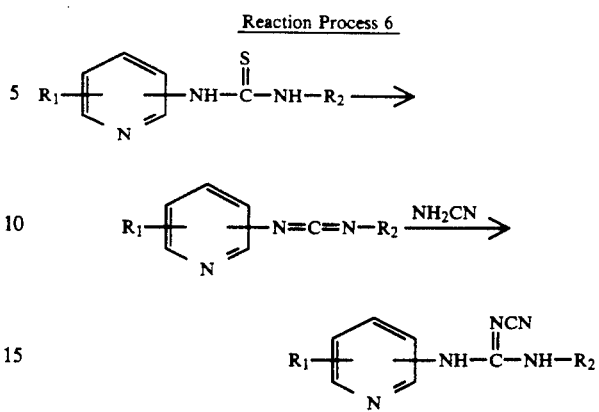

(when n is 0 and Z is NCN)

wherein $R_1$ and $R_2$ have the same meanings as given above.

First Step

The first step of this reaction process is conducted in an organic solvent such as dichloromethane, preferably in the presence of mercuric oxide, sulfur, triphenylphosphine, carbon tetrachloride or triethylamine at 30° to 60° C. for 10 to 100 hours.

Second Step

The second step of this reaction process is conducted in an organic solvent such as ether, preferably in the presence of diisopropylethylamine at 10° to 30° C. for 1 to 50 hours.

The novel compound (1) of the present invention thus produced can be collected as a product of arbitrary purity, appropriately using known separation and purification techniques such as concentration, extraction, chromatography, reprecipitation and recrystallization.

The compound (1) of the present invention has a basic group, so that it can be converted to the acid salt by techniques known in the art. There is no particular restriction on such a salt, as long as it is pharmaceutically acceptably non-toxic. Examples of such salts include inorganic acid salts (for example, hydrochlorides, hydrobromides, phosphates and sulfates) and organic acid salts (for example, acetates, succinates, maleates, fumarates, malates and tartrates).

The compounds (1) and the acid salts thereof of the present invention are very non-toxic, and have strong, sustained hypotensive, peripheral vasodilative, coronary vasodilative and cerebal vasodilative activities in mammals (for example, mice, rats, rabbits, dogs, cats and humans). They are therefore useful as prophylactic or therapeutic agents for circulatory diseases such as hypertension, ischemic heart diseases (for example, angina pectoris and myocardinal infarction) and cerebral and peripheral circulatory afflictions (for example, cerebral infarction and transient cerebral ischemic attack).

In particular, the compounds (1) and the acid salts thereof of the present invention are excellent in both the potency of the pharmacological action and the persistency thereof, compared to the conventional compounds having similar structures (for example, Pinacidil). For example, when they are used as prophylactic or therapeutic agents for hypertension, a stable hypotensive activity can be obtained by infrequent administration (once or twice a day).

Further, the compounds of the present invention are superior in a beneficial effect on blood lipids to Pinacidil. Therefore, the compounds of the present invention are expected to be useful for not only amelioration of lipometabolism but also relaxation of smooth muscle involved in gastrointestinal tract, respiratory system and uterus.

When the compounds (1) and the acid salts thereof of the present invention are used as the above-described drugs, pharmaceutically acceptable additives such as carriers, excipients and diluents are mixed with pharmaceutically required components to prepare medical compositions in powder, granule, tablet, capsule or injection form, which can be given orally or parenterally. The compounds (1) and the acid salts thereof of the present invention are contained in effective amounts thereof in the above-described preparations. The dosage varies depending on the administration route, the symptom, and the weight or the age of the patient. For example, when the preparations are orally given to adult patients with hypertension, it is desirable that the patients are dosed with 0.05 to 20 mg/kg of body weight/day, preferably with 0.1 to 4 mg/kg of body weight/day, administered once or in several divided doses.

The invention will be illustrated in more detail by reference to the following examples, but the invention is not limited to these examples.

EXAMPLE 1

(4-amino-3-pyridyl)thiourea hydrochloride

Thirty milliliters of concentrated hydrochloric acid was cooled with ice, and 3,4-diaminopyridine (10.0 g, 91.6 mmol) was added thereto. Then, the mixture was heated at 50° to 60° C. for 10 to 15 minutes, and thereafter excess hydrochloric acid was removed by distillation under reduced pressure. Ammonium thiocyanate (13.1 g, 0.17 mol) dissolved in 15 ml of water was added to the residue, followed by reaction at 80° C. for 4 hours. The reaction product was cooled to room temperature, and a precipitated solid was collected by filtration. The solid was washed with water and acetone, and dried to obtain a white solid (yield: 16.0 g).

IR (KBr): 3250, 3100, 3000, 1630 cm$^{-1}$
$^1$H-NMR (DMSO-d$_6$) δ ppm: 9.67 (1H, s), 8.40 (1H, s), 8.04 (1H, d, J=6.8 Hz), 8.35–7.45 (4H, brs), 6.96 (1H, d, J=7.2 Hz)
$^{13}$C-NMR (DMSO-d$_6$) δ ppm: 183.18, 156.00, 138.48, 137.10, 121.02, 109.43

EXAMPLES 2 To 8

3,4-Diaminopyridine (2 g, 18.3 mmol) was suspended in anhydrous pyridine (10 ml) under an atmosphere of nitrogen. Each of the isothiocyanates (R-NCS) shown in Table 1 was added dropwise thereto, followed by stirring. After removal of pyridine by distillation under reduced pressure, the reaction mixture was purified. When R is t-Bu, cyclo-Hex or CH(CH$_3$)C(CH$_3$)$_3$, the product was precipitated as a white powder. The powder was collected by filtration, and then washed with ether, followed by drying. Reaction conditions, purification methods and yields are shown in Table 1.

TABLE 1

| Example | R | Isothiocyanate (g, mmol) | Reaction Time (hr) | Yield (%) | Purification Method |
|---|---|---|---|---|---|
| 2 | Me[1] | (5.0, 68.7) | 14 | 94 | A |
| 3 | Et | (4.8, 55.0) | 21 | quantitative | B |
| 4 | n-Pr | (1.8, 18.3) | 5 days | 76 | B |
| 5 | n-Bu | (6.3, 55.0) | 42 | quantitative | B |
| 6 | t-Bu | (6.3, 55.0) | 7 days | 93 | C |
| 7 | c-C$_5$H$_{11}$ | (7.7, 55.0) | 40 | 93 | C |
| 8 | CH(CH$_3$)C(CH$_3$)$_3$ | (4.1, 28.8) | 5 days | 96 | C |

[1]Diaminopyridine (3 g, 27.5 mmol) was used.
A: Ether (20 ml) was added to the concentrated residue, and the resulting precipitate was collected by filtration.
B: The concentrated residue was purified by flash column chromatography (silica gel; 400 g/methanol).
C: The precipitated powder was collected by filtration.

The properties of the compounds obtained in Examples 2 to 8 and methods for preparation of the salts thereof are shown below.

EXAMPLE 2

(a) N-(4-amino-3-pyridyl)-N'-methylthiourea

IR (KBr): 3200, 1620, 1540, 1260 cm$^{-1}$
$^1$H-NMR (CDCl$_3$: MeOH-d$_4$=4:1) δppm: 8.02 (1H, d, J=5.6 Hz), 8.00 (1H, s), 6.68 (1H, d, J=5.6 Hz), 3.07 (3H, s)

(b) N-(4-amino-3-pyridyl)-N'-methylthiourea hydrochloride

Methanol (10 ml) was added to N-(4-amino-3-pyridyl)-N'-methylthiourea (1.02 g, 5.60 mmol) to prepare a homogeneous solution. Then, hydrochloric acid-ethanol (1.75 N, 3.2 ml) was added dropwise thereto under ice cooling and the resulting solution was stirred for 1 hour. A precipitate produced in the reaction mixture was collected by filtration, and dried at the reflux temperature of dichloromethane using a crystal dryer to obtain a monohydrochloride (816 mg) as a white powder.

m.p.: 278°–280° C.
IR (KBr): 3200, 1640, 1550, 1250 cm$^{-1}$
$^1$H-NMR (D$_2$O) δppm: 8.14 (1H, s), 8.04 (1H, dd, J=1.0 Hz, 7.0 Hz), 7.03 (1H, d, J=7.0 Hz), 3.04 (3H, s)
$^{13}$C-NMR (D$_2$O) δ ppm: 184.66, 160.69, 143.16, 141.35, 121.83, 112.84, 34.32

EXAMPLE 3

N-(4-amino-3-pyridyl)-N'-ethylthiourea

White powder

IR (KBr): 3200, 1640, 1540 cm$^{-1}$
$^1$H-NMR (DMSO-d$_6$) δppm: 9.20 (1H, s), 8.06 (1H, s), 8.06 (1H, s), 7.92 (1H, d, J=5.8 Hz), 6.70 (1H, d, J=5.8 Hz), 6.28 (2H, s), 3.45 (2H, q, J=6.3 Hz), 1.10 (3H, t, J=7.1 Hz)
$^{13}$C-NMR (DMSO-d$_6$) δ ppm: 181.73, 152.89, 143.21, 141.65, 120.76, 109.45, 38.88, 14.02

EXAMPLE 4

N-(4-amino-3-pyridyl)-N'-n-propylthiourea

White powder

IR (KBr): 3200, 1620, 1530, 1260 cm$^{-1}$
$^1$H-NMR (DMSO-d$_6$) δ ppm: 8.71 (1H, s), 7.91 (1H, s), 7.90 (1H, d, J=5.5 Hz), 7.51 (1H, s), 6.62 (1H, d, J=5.5 Hz), 5.70 (2H, s), 3.39 (2H, m), 1.54 (2H, sext, J=7.2 Hz), 0.87 (3H, t, J=7.4 Hz)

$^{13}$C-NMR (DMSO-d$_6$) δ ppm: 181.66, 150.47, 148.93, 147.22, 119.95, 109.72, 45.91, 21.85, 11.31

EXAMPLE 5

N-(4-amino-3-pyridyl)-N'-n-butylthiourea

White powder

IR (KBr): 3200, 1620 cm$^{-1}$ $^1$H-NMR (DMSO-d$_6$) δ ppm: 9.50 (1H, s), 8.37 (1H, s), 8.37 (1H, s), 7.97 (1H, d, J=6.1 Hz), 6.91 (2H, s), 6.83 (1H, d, J=6.1 Hz), 3.45 (2H, m), 1.59-1.25 (4H, m), 0.90 (3H, t, J=7.2 Hz) $^{13}$C-NMR (DMSO-d$_6$) δ ppm: 182.13, 152.78, 143.33, 141.83, 120.98, 109.52, 43.89, 30.64, 19.68, 13.81

EXAMPLE 6

(a) N-(4-amino-3-pyridyl)-N'-t-butylthiourea

White powder

IR (KBr): 3500, 2950, 1620, 1530, 1270 cm$^{-1}$ $^1$H-NMR (DMSO-d$_6$) δ ppm: 8.53 (1H, s), 7.94 (1H, s), 7.88 (1H, d, J=5.5 Hz), 7.22 (1H, s), 6.61 (1H, d, J=5.5 Hz), 5.70 (2H, s), 1.47 (9H,s)

$^{13}$C-NMR (DMSO-d$_6$) δ ppm: 181.02, 150.44, 149.26, 147.06, 120.66, 109.75, 52.72, 28.67

(b) N-(4-amino-3-pyridyl)-N'-t-butylthiourea dihydrochloride

Water (5 ml) was added to N-(4-amino-3-pyridyl)-N'-t-butylthiourea (962 mg, 4.29 mmol) to suspend it. 1 N aqueous solution of hydrochloric acid (8.58 ml) was added thereto, and the mixture was heated in a hot water bath until a homogeneous solution was obtained, followed by removal of water by distillation. The resulting white crystal was dried at the reflux temperature of dichloromethane using a crystal dryer to obtain a dihydrochloride (1.12 g) as a white powder. m.p.: >250° C.

IR (KBr): 3150, 1640, 1550, 1260 cm$^{-1}$

EXAMPLE 7

N-(4-amino-3-pyridyl)-N'-cyclohexylthiourea

White powder

IR (KBr): 3400, 1640, 1560 cm$^{-1}$

H-NMR (DMSO-d$_6$) δ ppm: 9.70 (1H, s), 8.58 (1H, d, J=7.6 Hz), 8.51 (1H, s), 8.03 (1H, d, J=6.7 Hz), 7.91 (1H, s), 6.96 (1H, d, J=6.7 Hz), 1.91 (2H, m), 1.70-1.56 (3H, m), 1.26 (5H, m)

$^{13}$C-NMR (DMSO-d$_6$) δ ppm: 180.83, 155.54, 138.16, 136.98, 121.24, 109.25, 52.48, 31.74, 24.21, 25.17

EXAMPLE 8

N-(4-amino-3-pyridyl)-N'-(1,2,3-trimethylpropyl)thiourea $^1$H-NMR (DMSO-d$_6$) δ ppm: 8.66 (1H, bs), 7.96 (1H, s), 7.89 (1H, d, J=5.5 Hz), 7.13 (1H, d, J=8.6 Hz), 6.62 (1H, d, J=5.5 Hz), 5.67 (2H, bs), 4.29 (1H, m), 1.05 (3H, d, J=6.7 Hz), 0.90 (9H, s)

$^{13}$C-NMR (DMSO-d$_6$) δ ppm: 181.81, 150.22, 148.88, 147.06, 120.51, 109.67, 57.46, 34.33, 26.19, 15.24

EXAMPLE 9 a) 4-Chloro-3-nitropyridine

Phosphorus oxychloride (25 ml, 0.27 mol) was added to 4-hydroxy-3-nitropyridine (7.0 g, 50.0 mmol), followed by reaction at 80° to 90° C. for 1.5 hours. Phosphorus oxychloride was removed by distillation. About 100 g of ice was added to the residue, and 28% aqueous ammonia was added dropwise thereto to adjust the pH to 7. Then, 100 ml of water was added thereto, and the aqueous mixture was extracted three times with 200 ml of dichloromethane. The resulting dichloromethane layer was dried, and then dichloromethane was removed by distillation under reduced pressure to obtain 7.75 g of a yellow liquid (yield: 97.8%).

(b) 3-Nitro-4-methylaminopyridine

Methylamine hydrochloride (1.55 g, 22.9 mmol) and potassium carbonate (4.22 g, 30.5 mmol) were added to a solution (5 ml) of 4-chloro-3-nitropyridine (2.3 g, 15.3 mmol) in dioxane. The mixture was stirred under reflux for 1.5 hours, at room temperature for 15 hours, and further under reflux for 3 hours. After filtration using Celite, the filtrate was concentrated and subjected to silica gel column chromatography (eluent: chloroform) to purify it, whereby 1.52 g of the intended product was obtained.

IR (CHCl$_3$): 3400, 2980, 1620, 1370 cm$^{-1}$ $^1$H-NMR (CDCl$_3$) δ ppm: 3.07 (3H, d, J=4.0 Hz), 6.72 (1H, d, J=6.0 Hz), 8.16 (1H, brs), 8.33 (1H, d, J=6.0 Hz), 9.21 (1H, s)

(c) 3-Amino-4-methylaminopyridine 150 mg of platinum oxide was added to 10 ml of a solution of 3-nitro-4-methylaminopyridine (1.5 g) in ethanol. The mixture was stirred under a hydrogen atmosphere at room temperature for 7.5 hours. Platinum oxide was removed by filtration, and the filtrate was concentrated. Thus, 962 mg (yield: 80%) of the intended product was obtained as brown crude crystals.

(d) N-(4-methylamino-3-pyridyl)-N'-cyclohexylthiourea

Cyclohexyl isothiocyanate (1.09 ml, 7.71 mmol) was added to a solution of 3-amino-4-methylaminopyridine (950 mg, 7.71 mmol) in DMF (5 ml), and the mixture was stirred at room temperature for 1 hour and at 120° C. for 3 hours. After removal of the solvent, the residue was subjected to silica gel column chromatography (eluent: chloroform:methanol=10:1 (v/v)) and recrystallization to purify it, thereby obtaining 98 mg of the intended product as flesh-colored crystals.

m.p.: >250° C.

IR (KBr): 3500-3000, 2920, 1600 cm$^{-1}$ $^1$H-NMR (CDCl$_3$) δ ppm: 1.0-2.1 (10H, m), 2.89 (3H, d, J=4.0 Hz), 4.1-4.4 (1H, m), 4.93 (1H, d, J=4.0 Hz), 5.72 (1H, d, J=6.0 Hz), 6.56 (1H, d, J=6.0 Hz), 7.65 (1H, s), 8.10 (1H, s), 8.26 (1H, d, J=6.0 Hz)

$^{13}$C-NMR (CDCl$_3$) δ ppm: 24.5, 25.1, 28.7, 32.2, 53.8, 105.2, 118.0, 147.4, 149.0, 151.7, 179.9

EXAMPLES 10 To 12

Using t-butylamine (Example 10), cyclohexylamine (Example 11) and diethylamine (Example 12) instead of methylamine used in Example 9 (b), 4-substituted amino-3-nitropyridine compounds corresponding thereto, respectively, were obtained. Then, the following corresponding aminopyridine compounds were obtained in accordance with the methods of Example 9 (c) and (d).

EXAMPLE 10

N-(4-t-butylamino-3-pyridyl)-N'-cyclohexylthiourea m.p.: 216°–218° C.

IR (KBr): 3500–3100, 2950, 2900, 1610 cm$^{-1}$ $^1$H-NMR (CDCl$_3$) δ ppm: 1.0–2.1 (19H, m), 4.1–4.4 (1H, m), 4.87 (1H, s), 6.78 (1H, d, J=6.0 Hz), 8.05 (1H, s), 8.13 (1H, d, J=6.0 Hz)

$^{13}$C-NMR (CDCl$_3$) δ ppm: 24.6, 24.7, 29.1, 32.5, 51.4, 54.0, 107.3, 118.9, 149.5, 180.3

EXAMPLE 11

N-(4-cyclohexylamino-3-pyridyl)-N'-cyclohexylthiourea m.p.: 157°–159° C.

IR (KBr): 3500–3000, 2900, 2800, 1600 cm$^{-1}$ $^1$H-NMR (CDCl$_3$) δ ppm: 1.0–2.1 (20H, m), 3.2–3.4 (1H, m), 4.1–4.4 (1H, m), 4.70 (1H, d, J=8.0 Hz), 5.72 (1H, brs), 6.57 (1H, d, J=6.0 Hz), 7.50 (1H, brs), 8.09 (1H, s), 8.19 (1H, d, J=6.0 Hz)

EXAMPLE 12

N-(4-diethylamino-3-pyridyl)-N'-cyclohexylthiourea m.p. 119°–121° C.

IR (KBr): 2900, 2800, 1595 cm$^{-1}$ $^1$H-NMR (CDCl$_3$) δ ppm: 1–2.5 (16H, m), 3.33 (4H, q), 4.1–4.4 (1H, m), 6.00 (1H, d, J=8.0 Hz), 6.76 (1H, d, J=6.0 Hz), 7.87 (1H, brs), 8.21 (1H, s), 8.23 (1H, d, J=6.0 Hz)

$^{13}$C-NMR (CDCl$_3$) δ ppm: 12.7, 24.7, 25.3, 32.6, 45.1, 112.8, 54.2, 121.9, 148.9, 150.1, 151.0, 179.4

EXAMPLE 13

(a) 4-(1-Imidazolyl)-3-nitropyridine

4-Chloro-3-nitropyridine (2.00 g, 12.6 mmol) and imidazole (2.25 g, 33.0 mmol) were dissolved in 10 ml of 1,4-dioxane, and 2 ml of triethylamine was added thereto, followed by reaction at 90° to 100° C. for 1.5 hours. Then, the solvent was removed by distillation under reduced pressure, and the residue was purified by silica gel column chromatography [eluent: dichloromethane:methanol=10:1 (v/v)] to obtain 2.31 g of a yellow liquid (yield: 96.4%).

$^1$H-NMR (DMSO-d$_6$) δ ppm: 9.32 (1H, s), 9.00 (1H, d, J=5.3 Hz), 8.08 (1H, s), 7.84 (1H, d, J=5.3 Hz), 7.53 (1H, s), 7.16 (1H, s)

(b) 3-Amino-4-(1-imidazolyl)pyridine 4-(1-Imidazolyl)-3-nitropyridine (2.10 g, 11.0 mmol) was dissolved in 20 ml of ethanol. After the atmosphere was replaced with nitrogen, 0.25 g of 10% palladium-carbon was added thereto. After the atmosphere was replaced with hydrogen, hydrogen addition was conducted with stirring at room temperature for 3 days. Palladium-carbon was removed by filtration and the filtered cake was washed with ethanol. The filtrate and the washings were combined and then concentrated. The residue was purified by silica gel column chromatography [eluent: dichloromethane: methanol=8:1–6:1 (v/v)] to obtain 1.62 g of a light brown solid (yield: 91.6%).

$^1$H-NMR (DMSO-d$_6$) δ ppm: 8.25 (1H, s), 7.92 (1H, s], 7.87 (1H, d, J=5.1 Hz), 7.44 (1H, s), 7.14 (1H, s), 7.11 (1H, d, J=5.1 Hz), 5.50–5.20 (2H, brs)

(c) N-4-(1-imidazolyl)-3-pyridyl]-N'-cyclohexylthiourea

3-Amino-4-(1-imidazolyl)pyridine (1.00 g, 5.95 mmol) was added to 5 ml of DMF, and cyclohexyl isothiocyanate (2.5 ml, 17.63 mmol) was added thereto. After reaction at room temperature for 4 days, the reaction solution was directly purified by column chromatography eluent: dichloromethane:methanol=7:1 (v/v)]. Ether was added to the collected effluent to achieve crystallization, and 0.30 g of the precipitated solid was collected by filtration (yield: 16.7%).

IR (KBr) 3150, 2900, 2850, 1590, 1550, 1500, 1080 cm$^{-1}$ $^1$H-NMR (DMSO-d$_6$) δ ppm:
9.10–8.90 (1H, brs), 8.57–8.50 (2H, s+d), 7.99 (1H, s), 7.98–7.85 (1H, brs), 7.55 (1H, d, J=5.3 Hz), 7.48 (1H, s), 7.11 (1H, s) 4.20–3.80 (1H, brs), 2.00–1.00 (10H, m)

$^{13}$C-NMR (DMSO-d$_6$) δ ppm: 181.37, 152.54, 148.49, 140.48, 136.59, 129.34, 128.17, 119.04, 118.55, 52.81, 31.71, 25.02, 24.45

EXAMPLE 14

(a) 4-Phenylamino-3-nitropyridine

4-Chloro-3-nitropyridine (1.50 g, 9.46 mmol) and aniline (2.0 ml, 21.9 mmol) were dissolved in 10 ml of 1,4-dioxane, and 2 ml of triethylamine was added thereto, followed by reaction at 80° to 90° C. for 2 hours. Then, the solvent was removed by distillation under reduced pressure, and 10 ml of hexane was added to the residue to wash it. The solvent was removed by decantation. The residue was further similarly treated with 10 ml of ether. The residue was purified by silica gel column chromatography [eluent: hexane:ethyl acetate=2:1 (v/v)]to obtain 1.41 g of a yellow solid (yield: 68.8%).

$^1$H-NMR (DMSO-d$_6$) δ ppm: 9.84 (1H, brs), 9.10 (1H, s), 8.24 (1H, d, J=6.2 Hz), 7.55–7.28 (5H, m), 6.88 (1H, d, J=6.2 Hz)

(b) 3-Amino-4-phenylaminopyridine

4-Phenylamino-3-nitropyridine (1.40 g, 6.51 mmol) was dissolved in the mixed solvent of 15 ml of ethanol and 10 ml of dichloromethane. After the atmosphere was replaced with nitrogen, 0.10 g of 10% palladium-carbon was added thereto. After the atmosphere was replaced with hydrogen, hydrogen addition was conducted with stirring at room temperature for about 15 hours. Palladium-carbon was removed by filtration and the filtered cake was washed with ethanol. The filtrate and the washings were combined and then concentrated. The residue was purified by silica gel column chromatography [eluent: dichloromethane: methanol=2:1 (v/v)]to obtain 1.07 g of a light brown solid (yield: 88.7%).

$^1$H-NMR (DMSO-d$_6$) δ ppm: 7.89 (1H, s), 7.64 (1H, d, J=5.4 Hz), 7.58 (1H, brs), 7.35–6.89 (6H, m), 5.20–4.70 (2H, brs)

(c) N-(4-phenylamino-3-pyridyl)-N'-cyclohexylthiourea

3-Amino-4-phenylaminopyridine (1.00 g, 5.40 mmol) was dissolved in 6 ml of DMF, and cyclohexyl isothiocyanate (1.0 ml, 6.8 mmol) was added thereto. The temperature was gradually raised, and reaction was conducted at 60° C. for 1.5 hours. Cyclohexyl isothiocyanate (0.5 ml, 3.4 mmol) was further added thereto, followed by reaction at 60° C. for 1.5 hours. After removal of the solvent by distillation under reduced pressure, the residue was purified by column chromatography [eluent: ethyl acetate]. The fractions containing the intended product, determined by thin layer chromatography, were subjected to recrystallization from methanol-dichloromethane-ether to obtain 1.23 g of a white solid (yield: 69.8%).

m.p.: 179°-182° C. (decomposed)

IR (KBr): 3150, 2900, 2850, 1590, 1500 cm$^{-1}$ $^1$H-NMR (DMSO-d$_6$) δ ppm: 8.80–8.70 (1H, brs), 8.30–8.15 (1H, brs), 8.04 (1H, d, J=5.6 Hz) 7.90 (1H, s), 7.80–7.55 (1H, brs), 7.45–6.90 (6H, m), 4.20–3.90 (1H, brs), 2.10–1.10 (10H, m)

$^{13}$C-NMR (DMSO-d$_6$) δ ppm: 180.57, 149.17, 147.05, 146.08, 140.37, 129.15, 123.35, 122.84, 120.98, 108.50, 52.71, 31.90, 25.13, 24.53

(d)

N-(4-phenylamino-3-pyridyl)-N'-cyclohexylthiourea hydrochloride

N-(4-phenylamino-3-pyridyl)-N'-cyclohexylthiourea (1.13 g, 3.46 mmol) was dissolved in 50 ml of ethanol, and 1.2 N hydrogen chloride-ethanol (3.0 ml, 3.6 mmol) was added thereto, followed by removal of the solvent by distillation. Then, ether was added to the residue to perform solidification, and thereafter removed by decantation. The resulting solid was dried to obtain 1.04 g of a white solid (yield: 82.8%).

IR (KBr): 3300, 2900, 1640, 1590, 1510 cm$^{-1}$ $^1$H-NMR (DMSO-d$_6$) δ ppm: 15.4–13.1 (1H, brs), 9.93 (1H, brs), 9.87 (1H, brs), 8.70 (1H, s), 8.57 (1H, brd, J=7.7 Hz), 8.14 (1H, d, J=7.0 Hz), 7.60–7.25 (5H, m), 7.05 (1H, d, J=6.9 Hz), 4.20–4.00 (1H, brs), 2.10–1.10 (10H, m)

$^{13}$C-NMR (DMSO-d$_6$) δ ppm: 180.70, 152.27, 138.10, 137.47, 137.07, 129.64, 126.58, 124.40, 123.23, 106.97, 52.49, 31.69, 25.16, 24.18

EXAMPLE 15

(a) 4-Pyrrolidine-1-yl-3-nitropyridine

4-Chloro-3-nitropyridine (2.02 g, 12.7 mmol) was suspended in 15 ml of 1,4-dioxane. The suspension was cooled a little in an ice bath, and then pyrrolidine (2.1 ml, 25.3 mmol) was added dropwise thereto. The temperature of the suspension was returned to room temperature, and the suspension was stirred for 30 minutes, followed by removal of the solvent by distillation under reduced pressure. The residue was purified by silica gel column chromatography (eluent: ethyl acetate) to obtain 2.34 g of a yellow solid (yield: 95.4%).

$^1$H-NMR (CDCl$_3$) δ ppm: 8.72 (1H, s), 8.23 (1H, d, J=6.2 Hz), 6.70 (1H, d, J=6.2 Hz), 3.40–3.20 (4H, m), 2.10–1.95 (4H, m)

(b) 3-Amino-4-pyrrolidine-1-yl-pyridine 4-pyrrolidine-1-yl-3-nitropyridine (2.10 g, 10.9 mmol) was dissolved in 40 ml of 1,4-dioxane. After the atmosphere was replaced with nitrogen, 0.42 g of 10% palladium-carbon was added thereto. After the atmosphere was replaced with hydrogen, hydrogen addition was conducted with stirring at room temperature for about 15 hours. Palladium-carbon was removed by filtraton and the filtered cake was washed with 1,4-dioxane. The filtrate and the washings were combined and then concentrated to obtain 1.61 of a brown liquid (yield: 90.7%).

$^1$H-NMR (DMSO-d$_6$) δ ppm: 7.80 (1H, s), 7.65 (1H, d, J=5.2 Hz), 6.53 (1H, d, J=5.3 Hz), 4.70–4.20 (2H, brs), 3.30–3.10 (4H, m), 2.00–1.75 (4H, m)

(c)

N-(4-pyrrolidine-1-yl-3-pyridyl)-N'-cyclohexylthiourea

3-Amino-4-pyrrolidine-1-yl-pyridine (1.55 g, 5.40 mmol) was dissolved in 10 ml of dichloromethane, and cyclohexyl isothiocyanate (2.6 ml, 18.3 mmol) was added thereto. Since a solid was precipitated, 2 ml of DMF was added thereto to dissolve the solid, and 2 ml of triethylamine was further added, followed by reaction at room temperature for 3 days. The solvent was removed by distillation under reduced pressure, and then the residue was purified by column chromatography [eluent: dichloro-methane:methanol=10:1–8:1 (v/v)]. The collected solid was recrystallized from dichloromethane to obtain 1.21 g of a light yellow solid (yield: 41.8%).

IR (KBr): 3150, 2950, 2850, 1600, 1510 cm$^{-1}$ $^1$H-NMR (DMSO-d$_6$) δ ppm: 9.00–8.60 (1H, brs), 7.97 (1H, d, J=5.8 Hz), 7.86 (1H, s), 7.40–6.80 (1H, brs), 6.51 (1H, d, J=5.9 Hz), 4.25–3.90 (1H, brs), ca. 3.4 (4H), 2.10–1.00 (14H, m)

$^{13}$C-NMR (DMSO-d$_6$) δ ppm: 181.20, 151.44, 149.78, 147.66, 119.34, 109.08, 52.65, 48.39, 32.00, 25.07, 24.56

EXAMPLE 16

(a) 3-Nitro-4-aminopyridine

Five grams (31.5 mmol) of 3-nitro-4-chloropyridine was mixed with 26 g of ammonium acetate, and the mixture was heated at 130–140° C. for 3 hours. The mixture was allowed to cool, and then adjusted to pH 10 with concentrated aqueous ammonia. The precipitated powder was collected by filtration to obtain 2.6 g of the intended yield: 59%).

(b) 3-Nitro-4-acetylaminopyridine

In 6 ml of pyridine, 1.2 g (8.63 mmol) of the amino compound of the above-described compound (a) was suspended, and then 0.65 ml (8.63 mmol) of acetyl chloride was gradually added under ice cooling. After reaction at room temperature for 24 hours, the solvent was removed by distillation. The residue was purified by silica gel column chromatography (eluent: chloroform:methanol=50:1) to obtain 1.12 g of the intended product (yield: 72%).

IR (KBr): 3350, 1720, 1600, 1350 cm$^{-1}$ (c) 3-Amino-4-acetylaminopyridine

To 40 ml of a solution of the acetylamide compound (1 g) of the above-described compound (b) in ethanol was added 200 mg of 10% palladium-carbon, followed by reaction in an atmosphere of hydrogen at room temperature for 24 hours. Palladium-carbon was removed by filtration, and then the solvent was removed by distillation to obtain the intended product (900 mg).

IR (KBr) 3300, 1695 cm$^{-1}$ (d) N-cyclohexyl-N'-(4-acetylamino-3-pyridyl)thiourea To 10 ml of a solution of the acetylamino compound (0.9 g, 5.95 mmol) of the above-described compound (c) in pyridine was added 0.84 ml (5.95 mmol) of cyclohexyl isothiocyanate, followed by reaction at room temperature for 48 hours and at 50°–60° C. for 14 hours. The solvent was removed by distillation, and the residue was washed with methanol to obtain 1 g of the intended product (yield: 57%).

IR (KBr): 3200, 2850, 1680 cm$^{-1}$ $^1$H-NMR (DMSO-d$_6$) δ ppm: 9.61 (1H, bs), 8.61 (1H, bs), 8.48 (1H, s), 8.25 (1H, d, J=5.4 Hz), 7.97 (1H, d, J=5.2 Hz), 7.79 (1H, d, J=5.4 Hz), 4.07 (1H, m), 2.13 (3H, s), 1.96–1.92 (2H, m), 1.70–1.57 (3H, m), 1.34–1.17 (5H, m)

$^{13}$C-NMR (DMSO-d$_6$) δ ppm: 180.67 (s), 169.32 (s), 149.73 (d), 146.46 (d), 140.12 (s), 126.54 (s), 116.06 (d), 52.89 (d), 31.84 (t), 25.12 (t), 24.56 (t), 23.93 (q)

EXAMPLE 17

N-cyclohexyl-N'-(4-benzoylamino-3-pyridyl)thiourea

The above-described compound was synthesized in accordance with the method described in Example 16 except for using benzoyl chloride in place of acetyl chloride used in Example 16(b).

IR (KBr): 3200, 2900, 1650 cm$^{-1}$ $^1$H-NMR (DMSO-d$_6$) δ ppm: 9.89 (1H, bs), 8.85 (1H, bs), 8.52 (1H, s), 8.39 (1H, d, J=5.4 Hz), 8.15 (1H, bs), 7.95 (2H, d, J=6.9 Hz), 7.85 (1H, d, J=5.4 Hz), 7.68–7.51 (3H, m), 4.10 (1H, bs), 1.92 (2H, m), 1.67–1.55 (3H, m), 1.33–1.21 (5H, m)

$^{13}$C-NMR (DMSO-d$_6$) δ ppm: 180.48 (s), 165.34 (s), 149.42 (d), 147.18 (d), 140.54 (s), 133.62 (s), 132.29 (d), 128.56 (d), 127.56 (d), 117.08 (d), 52.90 (d), 31.76 (t), 25.05 (t), 24.47 (t)

EXAMPLE 18

N-(2-amino-3-pyridyl)-N'-cyclohexylthiourea 2,3-Diaminopyridine (1.00 g, 9.16 mmol) was dissolved in 5 ml of pyridine, and cyclohexyl isothiocyanate (4.2 ml, 29.6 mmol) was added thereto. After reaction at room temperature for 4 days, pyridine was removed by distillation, and the residue was purified by silica gel column chromatography [eluent: chloroform:methanol=10:1 (v/v)]. Recrystallization from ethanol-ether-hexane gave 1.06 g of the intended product as white crystals (yield: 46.2%).

m.p.: 159°–160° C. (decomposed)

IR (KBr): 3350, 3250, 3100, 2900, 2850, 1630, 1520, 1500, 1460 cm$^{-1}$ $^1$H-NMR (CDCl$_3$) δ ppm 8.50 (1H, brs), 8.00 (1H, dd, J=5.0, 1.7 Hz), 7.36 (1H, dd, J=7.6, 1.6 Hz), 6.68 (1H, dd, J=7.6, 5.0 Hz), 5.70–5.55 (1H, brd), 5.50–4.90 (2H, brs), 4.33–4.10 (1H, brt), 2.10–0.95 (10H, m)

$^{13}$C-NMR (CDCl$_3$): δ ppm: 179.30, 155.68, 148.11, 136.62, 116.14, 114.28, 53.99, 32.46, 25.22, 24.62

EXAMPLES 19 And 20

Using 3,5-diaminopyridine (Example 19) and 2,5-diaminopyridine (Example 20) in place of 2,3-diaminopyridine, the following compounds were synthesized in accordance with the method described in Example 18.

EXAMPLE 19

N-(5-amino-3-pyridyl)-N'-cyclohexylthiourea m.p.: 114°–116° C.

IR (KBr): 3600–3000, 2900, 2850, 1600 cm$^{-1}$ $^1$H-NMR (DMSO-d$_6$) δ ppm: 1.0–2.0 (10H, m), 3.9–4.2 (1H, m), 5.31 (2H, brs), 7.21 (1H, s), 7.65 (1H, s), 7.66 (1H, s), 7.68 (1H, s), 9.19 (1H, s)

$^{13}$C-NMR (DMSO-d$_6$) δ ppm: 24.5, 25.1, 31.8, 52.1, 114.0, 131.7, 136.4, 144.6, 179.3

EXAMPLE 20

N-(6-amino-3-pyridyl)-N'-cyclohexylthiourea m.p.: 147°–149° C.

IR (KBr): 3500–3000, 2900, 2850, 1630, 1600 cm$^{-1}$ $^1$H-NMR (DMSO-d$_6$) δ ppm: 1.0–2.0 (10H, m), 3.40 (1H, brs), 4.05 (1H, brs), 5.80 (2H, brs), 6.41 (1H, d, J=8.0 Hz), 7.30 (1H, dd, J=2.0 Hz, 8.0 Hz), 7.74 (1H, d, J=2.0 Hz), 8.85 (1H, brs)

$^{13}$C-NMR (DMSO-d$_6$) δ ppm: 24.5, 25.1, 31.9, 52.3, 107.2, 125.1, 135.4, 144.4, 157.3, 180.4

EXAMPLE 21

N-(6-amino-3-pyridyl)-N'-1,2,2-trimethylpropylthiourea

Using 2,5-diaminopyridine in place of 3,4-diaminopyridine, the above-described compound was synthesized in accordance with the method described in Example 8.

IR (KBr) 3300, 2950, 1500 cm$^{-1}$ $^1$H-NMR (CDCl$_3$) δ ppm: 0.85 (9H, s), 1.08 (3H, d, J=6.7 Hz), 4.39 (1H, m), 4.80 (2H, brs), 5.55 (1H, d, J=9.3 Hz), 6.55 (1H, d, J=8.6 Hz), 7.25–7.40 (1H, m), 7.73 (1H, brs), 7.95 (1H, d, J=2.6 Hz)

$^{13}$C-NMR (DMSO-d$_6$) δ ppm: 15.3 (q), 26.3 (q), 34.3 (s), 57.2 (d), 107.2 (d), 125.2 (s), 135.4 (d), 144.3 (d), 157.3 (s), 181.6 (s)

EXAMPLE 22

(a)

S-methyl-N-(4-amino-3-pyridyl)-N'-cyanoisothiourea 3,4-Diaminopyridine (4 g, 36.6 mmol) was suspended in anhydrous pyridine (100 ml), and S,S'-dimethyl N-cyanodithioiminocarbonate (8.0 g, 55.0 mmol) was added thereto. The mixture was stirred at room temperature for 4 days. The resulting powder was collected from the reaction mixture by filtration, and washed with ether (100 ml) to obtain crude crystals. The crystals were purified by recrystallization from methanol-ether to obtain 1.91 g of the intended product as a white powder (yield: 58%). On the other hand, the filtrate was concentrated under reduced pressure, and the residue was purified by flash column chromatography (silica gel, eluent: chloroform:methanol=4:1 (v/v)) to obtain 2.8 g of the intended product (total yield: 95%).

(b)

N''-cyano-N'-(4-amino-3-pyridyl)-N-cyclohexylcuanidine

Cyclohexylamine (15 ml) was added to the methylthio compound (2.0 g, 9.65 mmol) obtained in (a). The mixture was stirred at room temperature for 6 hours, followed by heating to 70° C., and further stirred for 24 hours. Excess cyclohexylamine was removed from the reaction mixture by distillation under reduced pressure, and then the residue was purified by recrystallization from methanol-ether to obtain 1.4 g of the intended product as a white powder (yield: 56%). Recrystallization from methanol-ether was further conducted.

IR (KBr): 3300, 3150, 2900, 2190, 1630 cm$^{-1}$ $^1$H-NMR (DMSO-d$_6$) δ ppm: 8.22 (1H, s), 7.90 (1H, d, J=5.5 Hz), 7.84 (1H, s), 6.60 (1H, d, J=5.5 Hz), 5.19 (2H, s), 3.59 (1H, m), 1.06–1.80 (10H, m)

$^{13}$C-NMR (DMSO-d$_6$) δ ppm: 157.68, 150.66, 148.69, 147.57, 117.94, 117.41, 109.66, 50.45, 32.10, 24.96, 24.69

EXAMPLE 23

(a)
4-Amino-3-(1-methylthio-2-nitroethenylamino)pyridine 3,4-Diaminopyridine (6.00 g, 55.0 mmol) and 1,1-bis methylthio)-2-nitroethylene (10.0 g, 60.5 mmol) were dissolved in 60 ml of DMF and 10 ml of triethylamine, followed by reaction at 70° C. for 5 hours. The solvent was removed by distillation under reduced pressure, and the residue was purified by silica gel column chromatography [eluent: chloroform:methanol=2:1 (v/v)] to obtain 1.63 g of the intended product (yield: 13.1%)

$^1$H-NMR (DMSO-d$_6$) δ ppm: 8.00–7.87 (1H, brd), 7.75–7.85 (1H, brs), 6.60–6.85 (3H, brs+d), 6.53 (1H, s), 2.35 (3H, s)

(b)
4-Amino-3-(1-cyclohexylamino-2-nitroethenylamino)-pyridine

The compound obtained in (a) described above (1.60 g, 7.70 mmol) and cyclohexylamine (8.0 ml, 69.9 mmol) were heated at 80° C. for 2 hours, followed by removal of excess amine by distillation. The residue was purified by silica gel column chromatography [eluent: chloroform: methanol=2:1 (v/v)] (crude product: 1.0 g). The crude product was purified by HPLC (column: ODP-90 manufactured by Asahi Chemical Industry Co. Ltd., detection: 254 NM eluent: water: methanol=1:1 (v/v) to methanol) to obtain 180 mg of the intended product as a yellow solid (yield: 9.1%).

IR (KBr): 3400, 3200, 2900, 1600, 1540, 1390 cm$^{-1}$ $^1$H-NMR (DMSO-d$_6$) δ ppm: 10.50–10.0 (1H, brs), 9.00–8.40 (1H, brs), 7.98 (1H, d, J=5.6 Hz), 7.89 (1H, s), 6.66 (1H, d, J=5.6 Hz), 6.34–6.14 (2H, brs), 5.88–5.68 (1H, brs), 3.85–3.65 (1H, brs), 2.10–1.15 (10H, m)

$^{13}$C-NMR (DMSO-d$_6$) δ ppm: 155.78, 151.38, 148.97, 148.37, 117.16, 109.41, 97.84, 49.12, 32.12, 24.83, 23.95

EXAMPLE 24

N''-cyano-N-(6-amino-3-pyridyl)-N'-cyclohexylguanidine

Using 2,5-diaminopyridine in place of 3,4-diaminopyridine, the above-described compound was synthesized in accordance with the method described in Example 22.

Bright yellow crystals m.p.: 194°–196° C.

IR (KBr): 3600–3000, 2900, 2850, 2150, 1590 cm$^{-1}$ $^1$H-NMR (DMSO-d$_6$) δ ppm: 1.0–2.0 (10H, m), 3.4–3.8 (1H, m), 5.93 (2H, brs), 6.42 (1H, d, J=8.0 Hz), 6.53 (1H, d, J=8.0 Hz), 7.19 (1H, dd, J=1.0 Hz, 8.0 Hz), 7.70 (1H, d, J=1.0 Hz), 8.30 (1H, s)

$^{13}$C-NMR (DMSO-d$_6$) δ ppm: 24.8, 25.0, 32.1, 50.4, 107.8, 117.9, 122.8, 135.6, 145.2, 158.0

EXAMPLE 25

N''-cyano-N-(6-amino-3-pyridyl)-N'-(1,2,2-trimethylpropyl)-guanidine

Using 1,2,2-trimethylpropylamine in place of cyclohexylamine, the above-described compound was synthesized in accordance with the method described in Example 22(b).

Orange crystals m.p.: 175°–177° C.

IR (KBr): 3600–3000, 2950, 2150, 1600 cm$^{-1}$ $^1$H-NMR (DMSO-d$_6$) δ ppm: 0.84 (9H, s), 1.01 (3H, d, J=6.0 Hz), 3.6–3.9 (1H, m), 5.96 (2H, s), 6.10 (1H, d, J=10.0 Hz), 6.43 (1H, d, J=8.0 Hz), 7.19 (1H, dd, J=2.0 Hz, 8.0 Hz), 7.73 (1H, d, J=2.0 Hz), 8.55 (1H, s)

$^{13}$C-NMR (DMSO-d$_6$) δ ppm: 15.4, 26.1, 34.7, 55.0, 107.8, 117.2, 122.6, 135.4, 145.0, 158.0, 158.6

EXAMPLE 26

(a) 3-Nitro-6-pyridylcarbonitrile

3-Nitro-6-bromopyridine (5.62 g, 27.7 mmol) and CuCN (3.32 g, 35.7 mmol) were mixed with 6 ml of DMF, followed by reaction at 100°–110° C. for 2 hours. After cooling to room temperature, methylene chloride was added to the reaction mixture. Then, the mixture was stirred, followed by recovery of methylene chloride. After filtration using Celite, the filtrate was concentrated and purified by silica gel column chromatography (eluent: hexane:ethyl acetate=1:3 (v/v)) to obtain 2.74 g of a yellow solid (yield: 66%).

(b) 3-Amino-6-pyridylcarbonitrile

The nitropyridine compound (1.01 g) obtained in (a) described above was dissolved in 10 ml of dioxane, and 0.5 g of 10% palladium-carbon was added thereto. Then, the solution was vigorously stirred in an atmosphere of hydrogen at room temperature. Palladium-carbon was removed by filtration using Celite and the filtered cake was washed with ethanol. The filtrate and washings were combined and then concentrated. The residue was purified by silica gel column chromatography (eluent: hexane:ethyl acetate=1:3 (v/v)) to obtain 0.71 g of a light brown solid (yield: 88%).

(c) 3-Isothiocyanate-6-pyridylcarbonitrile

The aminopyridine compound (0.22 g, 1.85 mmol) obtained in (b) described above was suspended in 10 ml of toluene, and thiophosgene (0.16 ml, 2.1 mmol) was added thereto, followed by reflux for 1 hour. Toluene was removed by distillation, and the residue was extracted with methylene chloride. The extracted fractions was purified by silica gel column chromatography (eluent: hexane:ethyl acetate=4:1 (v/v)) to obtain 80 mg of an isothiocyanate as a yellow viscous liquid (yield: 27%).

(d)
N-(6-cyano-3-pyridyl)-N'-(1,2,2-trimethylpropyl)-thiourea

The isothiocyanate compound (80 mg, 0.5 mmol) obtained in (c) described above was dissolved in 1 ml of methylene chloride, and 1,2,2-trimethylpropylamine (0.15 ml, 1.12 mmol) was added thereto, followed by reaction at room temperature for several minutes. Then, the reaction mixture was purified by silica gel column chromatography (eluent: hexane:ethyl acetate=1:1 (v/v)) to obtain 0.13 g of a white solid (yield: 99%).

m p.: 146.0°–148.0° C.

IR (KBr): 3250, 3100, 2950, 2200, 1520 cm$^{-1}$ $^1$H-NMR (DMSO-d$_6$) δ ppm: 9.97 (1H, s), 8.79 (1H, d, J=2.4 Hz), 8.56 (1H, dd, J=8.6 Hz, 2.5 Hz), 7.99 (1H, d, J=9.2 Hz), 7.90 (1H, d, J=8.8 Hz), 4.40–4.20 (1H, m), 1.08 (3H, d, J=6.7 Hz), 0.93 (9H, s)

EXAMPLE 27

(a) 3-Amino-6-pyridinecarboxyamide

3-Amino-6-pyridinecarbonitrile (0.45 g) was mixed with 5 ml of methanol-3 N sodium hydroxide-35% aqueous hydrogen peroxide (2:3:1 (v/v)). After stirring at room temperature for 30 minutes, 5 ml of water was added to precipitate a solid. The precipitated solid was collected by filtration, and washed with water and acetone, followed by drying. Thus, 0.29 g of a white powder was obtained (yield: 56%).

(b) N-(6-carbamoyl-3-pyridyl)-N'-(1,2,2-trimethylpropyl)thiourea.

The carboxyamide compound (0.37 g, 27 mmol) obtained in (a) described above and 1,2,2-trimethylpropyl isothiocyanate (1.15 g, 8.03 mmol) were added to 2 ml of DMF, followed by reaction at 80°–90° C. for about 40 hours. DMF was removed by distillation, and the residue was purified by silica gel column chromatography (eluent: chloroform: methanol=13:1 (v/v)). Recrystallization from methanol-ether gave 0.4 g of the intended product (yield: 53%).

White solid
m.p.: 197°–199° C.
IR (KBr): 3200, 2900, 1690, 1530 cm$^{-1}$
$^1$H-NMR (DMSO-d$_6$) δ ppm: 9.77 (1H, s), 8.74 (1H, d, J=2.3 Hz), 8.32 (1H, dd, J=8.4 Hz, 2.1 Hz), 7.97 (2H, d+s, J=8.4 Hz), 7.82 (1H, d, J=9.2 Hz), 7.51 (1H, s), 4.45–4.25 (1H, m), 1.08 (3H, d, J=6.7 Hz), 0.94 (9H, s)

EXAMPLE 28

(a) 3-Nitro-6-methylaminopyridine

3-Nitro-6-chloropyridine (5 g, 31.5 mmol) was added to 10 ml of a 30% solution of methylamine in ethanol, followed by reaction at room temperature for 5 minutes. Then, recrystallization from chloroform-hexane gave 4.92 g of the intended product as yellow crude crystals.

(b) 3-Amino-6-methylaminopyridine

To 40 ml of an ethanol solution of the methylamino compound (4 g) obtained in (a) described above was added, 400 mg of platinum oxide, followed by reaction in an atmosphere of hydrogen at room temperature for 15 hours. The solvent was thereafter removed by distallation, and the residue was purified by silica gel column chromatography (eluent: chloroform, and subsequently chloroform: methanol=20:1 (v/v)) to obtain 320 mg of the intended product as brown crystals.

(c) N-(6-methylamino-3-pyridyl)-N'-(1,2,2-trimethylpropyl)thiourea 523 mg (3.65 mmol) of 1,2,2-trimethylpropyl isothiocyanate was added to 1.5 ml of a pyridine solution of the amino compound (300 mg, 2.44 mmol) obtained in (b) described above, and the mixture was stirred at room temperature for 18 hours. The precipitated crystals were collected by filtration, and washed with hexane and ether, followed by drying. Thus, 330 mg of the intended product was obtained (yield: 51%).

White crystals
m.p.: 195°–197° C.
IR (KBr): 3600–3000, 2950, 1620 cm$^{-1}$
$^1$H-NMR (CDCl$_3$) δ ppm: 0.85 (9H, s), 1.08 (3H, d, J=6.0 Hz), 2.96 (3H, d, J=5.0 Hz), 4.3–4.5 (1H, m), 4.9 (1H, brs), 5.58 (1H, d, J=6.0 Hz), 6.44 (1H, d, J=9.0 Hz), 7.31 (1H, dd, J=2.0 Hz, 9.0 Hz), 7.43 (1H, brs), 7.99 (1H, d, J=2.0 Hz)

$^{13}$C-NMR (DMSO-d$_6$) δ ppm: 15.4, 26.3, 28.2, 34.4, 57.2, 106.8, 124.9, 135.3, 144.1, 157.1, 181.7

Examples 29 TO 33

Using aniline (Example 29), ethylenediamine (Example 30), hydroxyethylamine (Example 31), imidazole (Example 32) and piperidine (Example 33) in place of methylamine, the following compounds were synthesized in accordance with the method described in Example 28.

EXAMPLE 29

N-(6-phenylamino-3-pyridyl)-N'-(1,2,2-trimethylpropyl)thiourea m.p.: 168°–170° C.
IR (KBr): 3500–3100, 3020, 2950, 1600, 1530 cm$^{-1}$
$^1$H-NMR (CDCl$_3$) δ ppm: 0.87 (9H, s), 1.09 (3H, d, J=6.0 Hz), 4.3–4.6 (1H, m), 5.60 (1H, d, J=8.0 Hz), 6.91 (1H, d, J=8.0 Hz), 7.01 (1H, s), 7.3–7.5 (6H, m), 7.65 (1H, s), 8.08 (1H, d, J=2.0 Hz)
$^{13}$C-NMR (DMSO-d$_6$) δ ppm: 15.3, 26.3, 34.4, 57.2, 109.9, 117.6, 120.2, 127.8, 128.6, 134.9, 141.8, 142.8, 152.9, 181.4

EXAMPLE 30

N-[6-(2-aminoethyl)amino-3-pyridyl]-N'-(1,2,2-trimethylpropyl)thiourea m.p.: 138°–140° C.
IR (KBr): 3600–3000, 2950, 1615, 1530 cm$^{-1}$
$^1$H-NMR (CDCl$_3$) δ ppm: 0.85 (9H, s), 1.08 (3H, d, J=6.0 Hz), 2.97 (2H, t, J=6.0 Hz), 3.3–3.5 (2H, m), 4.3–4.6 (1H, m), 5.27 (1H, brs), 5.56 (1H, d, J=8.0 Hz), 6.46 (1H, d, J=9.0 Hz), 7.28 (1H, dd, J=4.0 Hz, 9.0 Hz), 7.52 (1H, brs), 7.97 (1H, d, J=4.0 Hz)

EXAMPLE 31

N-[6-(2-hydroxyethylamino)-3-pyridyl]-N'-(1,2,2-trimethylpropyl)thiourea

IR (KBr): 3200, 3080, 3000, 2920, 1520, 1480, 1190 cm$^{-1}$
$^1$H-NMR (DMSO-d$_6$) δ ppm: 0.89 (7H, s), 1.03 (3H, d, J=6.6 Hz), 3.30 (2H, t, J=5.7 Hz), 3.53 (2H, t, J=5.7 Hz), 4.20–4.35 (1H, m), 4.60–4.75 (1H, br), 6.48 (1H, d, J=8.8 Hz), 6.48 (1H, s), 7.13 (1H, d, J=8.1 Hz), 7.38 (1H, dd, J=8.8 Hz, 2.1 Hz), 7.81 (1H, d, J=2.1 Hz), 9.00 (1H, s)

EXAMPLE 32

N-[6-(1-imidazolyl)-3-pyridyl]-N'-(1,2,2-trimethylpropyl)thiourea

IR (KBr): 3400–3200, 2900, 1610, 1180 cm$^{-1}$
$^1$H-NMR (DMSO-d$_6$) δ ppm: 0.93 (9H, s), 1.07 (3H, d, J=6.7 Hz), 4.25–4.40 (1H, m), 7.11 (1H, s), 7.73–7.77 (1H, brs), 7.75 (1H, d, J=8.7 Hz), 7.90 (1H, s), 8.28 (1H, dd, J=8.7 Hz, 2.5 Hz), 8.47 (1H, s), 8.50 (1H, d, J=2.5 Hz), 9.60 (1H, s)

EXAMPLE 33

N-(6-piperidino-3-pyridyl)-N'-(1,2,2-trimethylpropyl)thiourea m.p.: 151°–153° C.
IR (KBr): 3600–3000, 2900, 1600, 1535 cm$^{-1}$
$^1$H-NMR (CDCl$_3$) δ ppm: 0.86 (9H, s), 1.08 (3H, d, J=6.0 Hz), 1.66 (6H, brs), 3.57 (4H, brs), 4.3–4.6 (1H, m), 5.63 (1H, d, J=6.0 Hz), 6.67 (1H, d, J=8.0 Hz), 7.33 (1H, dd, J=2.0 Hz, 8.0 Hz), 7.53 (1H, brs), 8.05 (1H, d, J=2.0 Hz)

EXAMPLE 34

(a) 2-Hydrazino-5-nitropyridine

2-Chloro-5-nitropyridine (5 g, 31.5 mmol) and hydrazine (1.74 g, 34.7 mmol) were dissolved in 60 ml of dioxane, and the solution was stirred at room temperature for 16 hours. The precipitated yellow powder (m.p.: 198°–208°0 C.) was collected by filtration to obtain 502 mg of the intended product as a hydrochloride salt.

(b) 6-(2-t-butoxycarbonylhydrazino)-3-nitropyridine

2-Hydrazino-5-nitropyridine hydrochloride (1 g, 5.3 mmol) was suspended in the mixed solvent of 20 ml of dioxane, 1 ml of DMF and 2.5 ml of triethylamine, and 2.4 ml of di-t-butyl dicarbonate was added thereto with stirring. The reaction solution was refluxed for 2 hours. After completion of the reaction, the reaction solution was filtered. The solvent was removed from the reaction solution by distillation under reduced pressure, and the residue was purified by silica gel column chromatography (eluent: hexane:ethyl acetate=3:2 (v/v)) to obtain 1.27 g of the intended product as a yellow powder (m.p.: 132.5°–134° C.).

(c) 3-Amino-6-(2-t-butoxycarbonylhydrazino)pyridine 57 mg of platinum oxide was added to a solution of 6-(2-t-butoxycarbonylhydrazino)-3-nitropyridine (570 mg) in ethanol (10 ml). The mixture was vigorously stirred in an atmosphere of hydrogen at room temperature for 1 hour. After completion of the reaction, the reaction solution was filtered, and the filtered cake was thoroughly washed with ethanol. The filtrate and the washings were combined, and the solvent was removed by distillation to obtain 502 mg of 3-amino-6-(2-t-butoxycarbonylhydrazino)pyridine as a brown powder.

(d) N-[6-(2-t-butoxycarbonylhydrazino)-3-pyridyl]-N'-(1,2,2-trimethylpropyl)thiourea 3-Amino-6-(2-t-butoxycarbonylhydrazino)pyridine (500 mg, 2.2 mmol) and 1,2,2-trimethylpropyl isothiocyanate (351 mg, 2.5 mmol) were dissolved in 10 ml of pyridine, and the solution was stirred at room temperature for 16 hours. After completion of the reaction, the solvent was removed by distillation under reduced pressure, and the residue was purified by silica gel column chromatography (eluent: hexane:ethyl acetate=1:3 (v/v)) to obtain the powdery white intended product (m.p.: 143°–146° C.).

IR (KBr): 3250, 2950, 1690, 1530 cm$^{-1}$ $^1$H-NMR (DMSO-d$_6$) δ ppm: 0.90 (9H, s), 1.04 (3H, d, J=6 Hz), 1.42 (9H, s), 4.29 (1H, m), 6.48 (1H, d, J=8 Hz), 7.28 (1H, brd), 7.58 (1H, dd, J=2 Hz), 7.94 (1H, d, J=2.3 Hz), 8.07 (1H, s), 8.78 (1H, s), 9.08 (1H, s)

$^{13}$C-NMR (DMSO-d$_6$) δ ppm: 18.4 (q), 28.1 (q), 56.0 (q), 79.1 (d), 106.6 (d), 124.7 (d), 133.0 (d), 137.6 (s), 152.3 (s), 156.2 (s), 187.9 (s)

EXAMPLE 35

N-(6-hydrazino-3-pyridyl)-N'-(1,2,2-trimethylpropyl)thiourea hydrochloride 3.5 ml of 8.83 N solution of hydrochloric acid in ethanol was added to a solution of N-(6-t-butoxycarbonylhydrazino-3-pyridyl)-N'-(1,2,2-trimethylpropyl)thiourea (150 mg, 0.41 mmol) obtained in Example 34 in ethanol (2 ml). After stirring at room temperature for 30 minutes, the solution was stirred in an ice bath for 30 minutes. Then, the solution was allowed to stand in an ice bath for 30 minutes, The precipitated blue powder was collected by filtration, and dried to obtain 85 mg of the intended product.

IR (KBr): 3200, 1690, 1600, 1540 cm$^{-1}$ $^1$H-NMR (DMSO-d$_6$) δ ppm: 0.92 (9H, s), 1.04 (3H, d, J=6.7 Hz), 3.0–4.5 (1H, br), 4.26 (1H, q, J=6.7 Hz), 6.85 (1H, d, J=9 Hz), 7.85 (1H, dd, J=2.1 Hz, 9.0 Hz), 8.07 (1H, d, J=8.6 Hz), 8.27 (1H, s), 9.1–9.5 (1H, s), 10.07 (1H, s)

EXAMPLE 36

Using t-butoxycarbonyl-glycine-N-hydroxysuccinimide ester in place of di-t-butyl dicarbonate, the following compounds were obtained by the methods described in Example 34.

(a) N-6-(2-t-butoxycarbonylqlycylhydrazino)-3-pyridyl]-N'-(1,2,2-trimethylpropyl)thiourea IR (KBr) 3400, 1680 cm$^{-1}$ $^1$H-NMR (DMSO-d$_6$) δ ppm: 9.75 (1H, s), 9.09 (1H, s), 8.24 (1H, s), 7.95 (1H, d, J=2.1 Hz), 7.57 (1H, dd, J=2.0 Hz, 8.7 Hz), 7.31 (1H, d, J=9.3 Hz), 7.02 (1H, t), 6.57 (1H, d, J=8.8 Hz), 4.28 (1H, m), 3.62 (2H, d, J=5.9 Hz), 1.39 (9H, s), 1.04 (3H, d, J=6.6 Hz), 0.90 (9H, s)

(b) N-[6-(2-glycylhydrazino)-3-pyridyl]-N'-(1,2,2-trimethylpropyl)thiourea hydrochloride IR (KBr): 3400–3100, 1700 cm$^{-1}$ $^1$H-NMR (DMSO-d$_6$) δ ppm: 11.17 (1H, s), 10.74 (2H, s), 8.50 (1H, s), 8.47–8.39 (4H, m), 8.13 (1H, dd, J=2.1 Hz, 9.4 Hz), 7.20 (1H, d, J=9.4 Hz), 4.24 (1H, m), 3.86 (2H, d, J=5.3 Hz), 1.05 (3H, d, J=6.7 Hz), 0.93 (9H, s)

$^{13}$C-NMR (DMSO-d$_6$) δ ppm: 180.71 (s), 166.78 (s), 150.16 (s), 141.16 (d), 129.47 (d), 127.87 (s), 110.87 (d), 57.39 (d), 39.50 (t), 34.28 (s), 26.34 (q), 15.18 (q)

EXAMPLE 37

Using 4-ethoxycarbonylpiperazine in place of di-t-butyl dicarbonate, the following compounds were obtained by the methods described in Example 34.

(a) N-6-(4-ethoxycarbonyl-1-piperazinyl)-3-pyridyl]-N'-(1,2,2-trimethylpropyl)thiourea IR (KBr): 3200, 1690 cm$^{-1}$ $^1$H-NMR (CDCl$_3$) δ ppm: 8.08 (1H, d, J=2.6 Hz), 7.43 (1H, bs), 7.38 (1H, dd, J=2.6 Hz, 9.0 Hz), 6.67 (1H, d, J=8.9 Hz), 5.59 (1H, d, J=9.8 Hz), 4.40 (1H, m), 4.18 (2H, q, J=7.0 Hz), 3.60 (8H, s), 1.29 (3H, t, J=7.1 Hz), 1.08 (3H, d, J=6.7 Hz), 0.86 (9H, s)

(b) N-6-(4-ethoxycarbonyl-1-piperazinyl)-3-pyridyl]-N'-(1,2,2-trimethylpropyl)thiourea hydrochloride IR (KBr): 3250, 1700 cm$^{-1}$ $^1$H-NMR (CDCl$_3$) δ ppm: 10.74 (1H, bs), 9.01 (1H, d, J=9.0 Hz), 7.93 (1H, s), 7.83 (1H, d, J=9.1 Hz), 6.95 (1H, d, J=9.6 Hz), 4.35 (1H, m), 4.19 (2H, q, J=7.1 Hz), 3.75 (8H, m), 1.30 (3H, t, J=7.1 Hz), 1.17 (3H, d, J=6.7 Hz), 1.01 (9H, s)

$^{13}$C-NMR (CDCl$_3$) δ ppm: 181.24 (s), 155.04 (s), 149.04 (s), 143.45 (d), 129.86 (s), 128.22 (d), 110.09 (d), 62.00 (t), 58.45 (d), 46.71 (t), 42.54 (t), 34.55 (s), 26.47 (q), 15.29 (q), 14.54 (q)

EXAMPLE 38

(a) 2-Acetylamino-5-nitropyridine

To a solution of 2-amino-5-nitropyridine (4.0 g, 28.8 mmol) in dichloromethane (15 ml) were added 176 mg (31.6 mmol) of 4-N,N'-dimethylaminopyridine (DMAP), 4.41 ml of triethylamine (31.6 mmol) and 2.16 ml (31.6 mmol) of acetyl chloride in turn, and the mixture was stirred at room temperature for 1 hour. A 1 M aqueous solution of potassium carbonate was added to the mixed suspension to neutralize it. Extraction with chloroform was repeated three times, and the extract was dried over magnesium sulfate. The solvent was removed, and the residue was subjected to silica gel column chromatography (eluent: chloroform). Recrystallization from chloroform-hexane gave 2.14 g of the intended product as a flesh-colored powder (yield: 49%).

(b) 2-Acetylamino-5-aminopyridine 100 mg of platinum oxide was suspended in a solution of 2-acetylamino-5-nitropyridine (1.0 g, 5.52 mmol) in ethanol (20 ml). The suspension was stirred in an atmosphere of hydrogen at room temperature for 1.5 hours. Platinum oxide was removed by filtration using Celite, and the solvent was removed by distillation under reduced pressure. The residue was purified by silica gel column chromatography (eluent: chloroform alone to chloroform:methanol=10:1 (v/v)) to obtain 170 mg of the intended product as dark brown crude crystals (yield: 20%).

(c) N-(6-acetylamino-3-pyridyl)-N'-(1,2,2-trimethylpropyl)thiourea

To a solution of 2-acetylamino-5-aminopyridine (150 mg, 0.99 mmol) in pyridine (1.5 ml), 213 mg (1.49 mmol) of 1,2,2-trimethylpropyl isothiocyanate was added dropwise, followed by stirring at room temperature for 22 hours, at 50° C. for 5 hours and further at room temperature for 15 hours. Then, the solvent was removed by distillation under reduced pressure. The residue was recrystallized from chloroform-hexane to obtain 232 g of the intended product as a flesh-colored powder (yield: 79%).

m.p.: 197°-199° C.
IR (KRr): 3500-3000, 2950, 1670, 1590 cm$^{-1}$
$^1$H-NMR (DMSO-d$_6$) δ ppm: 0.92 (9H, s), 1.06 (3H, d, J=6.0 Hz), 2.08 (3H, s), 4.32 (1H, m), 7.53 (1H, d, J=8.0 Hz), 7.84 (1H, dd, J=1.0 Hz, 8.0 Hz), 8.01 (1H, d, J=8.0 Hz), 8.35 (1H, d, J=1.0 Hz), 9.35 (1H, s), 10.42 (1H, s)
$^{13}$C-NMR (DMSO-d$_6$) δ ppm: 15.2, 23.7, 26.3, 34.3, 57.2, 112.6, 132.1, 133.2, 142.8, 148.2, 168.8, 181.0

EXAMPLE 39

N-(6-benzoylamino-3-pyridyl)-N'-1,2,2-trimethylpropylthiourea

Using benzoyl chloride in place of acetyl chloride, the above-described compound was synthesized in accordance with the method described in Example 38.

m.p.: 168°-170° C.
IR (KBr): 3600-3000, 2950, 1650, 1610 cm$^{-1}$
$^1$H-NMR (CDCl$_3$) δ ppm: 0.87 (9H, s), 1.01 (3H, d, J=6.0 Hz), 4.25 (1H, brs), 7.3-7.6 (4H, m), 7.8-8.2 (4H, m), 8.41 (1H, s), 9.36 (1H, s), 10.68 (1H, s)

EXAMPLES 40 To 42

Using 2-methylpropyl isothiocyanate (Example 40), 1-dimethylpropyl isothiocyanate (Example 41) and exo-2-norbornyl isothiocyanate (Example 42) in place of 1,2,2-trimethylpropyl isothiocyanate, the following compounds were synthesized in accordance with the method described in Example 21.

EXAMPLE 40

N-(6-amino-3-pyridyl)-N'-(2-methylpropyl)thiourea

IR (KBr): 3300, 2950, 1550, 1350, 1280 cm$^{-1}$
$^1$H-NMR (CDCl$_3$) δ ppm: 0.88 (6H, d, J=6.7 Hz), 1.90 (1H, d, hept, J=6.9 Hz, 6.7 Hz), 3.43 (2H, dd, J=6.9 Hz, 5.7 Hz), 4.70 (2H, brs), 5.73 (1H, brs), 6.55 (1H, dd, J=8.6 Hz, 0.6 Hz), 7.32 (1H, dd, J=8.6 Hz, 2.6 Hz), 7.49 (1H, brs), 7.97 (1H, d, J=2.6 Hz)
$^{13}$C-NMR (DMSO-d$_6$) δ ppm: 20.1 (q), 27.5 (d), 51.4 (t), 107.5 (d), 124.7 (s), 135.7 (d), 144.8 (d), 157.6 (s), 181.8 (s)

EXAMPLE 41

N-(6-amino-3-pyridyl)-N'-(1,1-dimethylpropyl)thiourea

IR (KBr): 3180, 2950, 1630, 1530, 1250, 1190 cm$^{-1}$
$^1$H-NMR (CDCl$_3$) δ ppm: 0.82 (3H, t, J=7.5 Hz), 1.43 (6H, s), 1.90 (2H, q, J=7.5 Hz), 4.76 (2H, brs), 5.56 (1H, brs), 6.54 (1H, dd, J=8.7 Hz, 0.4 Hz), 7.31 (1H, dd, J=8.7 Hz, 2.6 Hz), 7.51 (1H, brs), 7.92 (1H, d, J=2.6 Hz)
$^{13}$C-NMR (DMSO-d$_6$) δ ppm: 8.2 (q), 26.5 (q), 32.0 (d), 55.2 (s), 107.3 (d), 125.1 (s), 135.9 (d), 144.4 (d), 157.3 (s), 180.9 (s)

EXAMPLE 42

N-(6-amino-3-pyridyl)-N'-(exo-2-norbornyl)thiourea

IR (KBr): 3350, 2950, 1630, 1520, 1400, 1280 cm$^{-1}$
$^1$H-NMR (CDCl$_3$) δ ppm:
1.00-1.75 (8H, m), 2.15-2.30 (2H, m), 3.70-4.05 (1H, m), 5.82 (2H, brs), 6.39 (1H, d, J=8.8 Hz), 7.32 (1H, dd, J=8.8 Hz, 2.5 Hz), 7.40 (1H, brs), 7.74 (1H, d, J=2.5 Hz), 8.77 (1H, brs)
$^{13}$C-NMR (DMSO-d$_6$) δ ppm: 26.0 (t), 27.9 (t), 35.1 (t), 38.9 (t), 35.2 (d), 41.7 (d), 56.8 (d), 107.1 (d), 125.4 (s), 135.5 (d), 144.5 (d), 157.3 (s), 180.9 (s)

EXAMPLE 43

(a) N-(6-amino-3-pyridyl)-N'-(exo-2-norbornyl)carbodiimide

To a solution of the thiourea compound (2 g, 7.62 mmol) of Example 42 in methylene chloride-ethanol (1:1 (v/v), 100 ml) were added 4.95 g (27.9 mmol) of mercuric oxide and 0.122 g (3.81 mmol) of sulfur, and the mixture was stirred at room temperature for 3 days. Mercuric oxide, mercuric sulfide and sulfur were filtered off using Celite, and the filtered cake was washed with methylene chloride. The filtrate and the washings were combined, and the solvent was removed by distillation to obtain 1.77 g of the intended product.

(b) N-(6-amino-3-pyridyl)-N''-cyano-N'-(exo-2-norbornyl)guanidine

To 20 ml of a methylene chloride solution of the carbodiimide compound (1.743 g, 7.63 mmol) obtained in (a) described above, 0.641 g (15.27 mmol) of cyanamide and a drop of N,N-diisopropylethylamine were added, and the mixture was stirred at room temperature for one day. The solvent was removed by distillation, and the residue was purified by silica gel column chromatography (eluent: chloroform:methanol=10:1 (v/v)), followed by recrystallization from methylene chloride-methanol-ether. Thus, 1.538 g of the intended product was obtained.

White powder m.p.: 180°–181° C.
IR (KBr): 3300, 2900, 2150, 1585, 1490, 1375 cm$^{-1}$
$^1$H-NMR (CDCl$_3$) δ ppm: 1.00–1.70 (8H, m), 2.10–2.25 (2H, m), 3.50–3.65 (1H, m), 5.92 (2H, brs), 6.41 (1H, d, J=8.6 Hz), 6.45 (1H, d, J=5.9 Hz), 7.18 (1H, dd, J=8.6 Hz, 2.6 Hz), 7.70 (1H, d, J=2.6 Hz), 8.44 (1H, brs)

EXAMPLE 44

(a)

N-[6-3-(3-benzyloxycarbonyl-5-oxo-4-oxazolidinyl)-propionylamino]-3-pyridyl]-N''-cyano-N'-(exo-2-norbornyl) guanidine To 922 mg of N-(6-amino-3-pyridyl)-N''-cyano-N'-(exo-2-norbornyl) guanidine obtained in Example 43 were simultaneously added dropwise a solution (: ml) of 3-(S) -(3-benzyloxycarbonylbornyl-5-oxo-4-oxazolidinyl)propionyl-chloride (1.06 g, 3.41 mmol) in DMF and a solution (1 ml) of triethylamine (0.475 ml) in DMF. After completion of the dropping, the mixture was stirred at room temperature for 16 hours. After completing the reaction, the solvent was removed from the reaction mixture by distillation under reduced pressure, and then the residue was purified by silica gel chromatography [eluent: methanol:chloroform=1:20 (v/v)] to obtain 394 mg of the intended product (yield: 21.2%).

(b)

N-[6-(benzyloxycarbonyl-γ-L-glutamylamino)-3-pyridyl]-N''-cyano-N'-(exo-2-norbornyl) guanidine

[6-[3-(3-benzyloxycarbonyl-5-oxo-4-oxazolidinyl)-propionylamino]-3-pyridyl]-N''-cyano-N'-(exo-2-norbornyl) guanidine (410 mg, 0.76 mmol) was dissolved in 15 ml of THF and 0.75 ml of 1N sodium hydroxide was added thereto with stirring at room temperature. The mixture was stirred at room temperature for 20 minutes, followed by removal of the solvent by distillation under reduced pressure. The residue was purified by silica gel chromatography [eluent: methanol:chloroform=1:2 (v/v)]to obtain 370 mg of the intended product (yield: 92.3%).

N-[6-(γ-L-glutamylamino)-3-pyridyl-N''-cyano-N'-(exo-2-norbornyl) guanidine

N-[6-(benzyloxycarbonyl-γ-L-glutamylamino)-3-pyridyl]-N''-cyano-N'-(exo-2-norbornyl) guanidine (20 mg, 0.0375 mmol) and 4 mg of lithium hydroxide were added to 1 ml of water. After atmosphere was completely replaced with nitrogen, palladium-carbon was added to the mixture. Then the atmosphere was replaced with hydrogen and the mixture was vigorously stirred in an atmosphere of hydrogen at room temperature for 2 hours. After completion of the reaction, the reaction mixture was filtered and the filtrated cake was thoroughly washed with water. The filtrate and the washings were combined, and the solution was neutralized with 1N-hydrochloric acid, followed by removal of the solvent by distillation. The residue was purified by HPLC to obtain 6 mg of the intended product as a white powder (yield: 40%).

m.p. 200°–204° C. IR (KBr): 3200, 2950, 2200, 1680 cm$^{-1}$
$^1$H-NMR (DMSO-d$_6$) δ ppm: 10.7 (1H, br), 8.15 (1H, d, J=2.6 Hz), 7.99 (1H, d, J=8.9 Hz), 7.79 (1H, br), 7.60 (1H, dd, J=2.6, 8.9 Hz), 3.70 (1H, br), 3.27 (1H, t, J=6.3 Hz), 2.50 (2H, br), 2.21 (2H, br), 1.91 (2H, q, J=6.3 Hz), 1.00–1.80 (8H, m)

EXAMPLES 45 To 50

Using N-(6-amino-3-pyridyl)-N''-cyano-N'(exo-2-norbornyl)guanidine as a starting material, the compounds of Examples 45 to 49 were obtained using the following reagents by the following methods:

| Example No. | Reagent | Method |
|---|---|---|
| 45 | benzyloxycarbonyl alanine | DDC condensation |
| 46 | ethyl chloroformate | see Example 38 |
| 47 | benzyl chloroformate | see Example 38 |
| 48 | n-hexyl isocyanate | see Example 38 |
| 49 | 6-(5-methyl-2-oxo-2H-1,3-dioxole-4-yl)methyl chloride | standard N-alkylation |

The compounds of Example 50 was obtained in accordance with the method in Example 28 by using 2-oxopropylamine ethylene ketal and exo-2-norbornyl isothiocyanate in place of methylamine and 1,2,2-trimethylpropyl isothiocyanate respectively. Hydrochlorides of Example 46 and 47 were obtained by a conventional method such as Example 14(c) and (d).

EXAMPLE 45

N-(6-L-alanylamino-pyridyl)-N''-cyano-N'-(exo-2-norbornyl) guanidine

White Powder m.p. 154.0°–158° C.
$^1$H-NMR (DMSO-d$_6$) δ ppm: 8.15 (1H, d, J=2.7 Hz), 8.07 (1H, d, J=8.9 Hz), 7.62 (1H, dd, J=8.9, 2.7 Hz), 7.02 (1H, d, J=6.5 Hz), 3.55–3.75 (1H, m), 3.51 (1H, q, J=6.8 Hz), 3.0–3.9 (2H, br), 2.15–2.30 (2H, m), 1.23 (3H, d, J=6.8 Hz), 1.00–1.80 (8H, m)

EXAMPLE 46

N-(6-ethoxycarbonylamino-3-pyridyl)-N''-cyano-N'-(exo-2-norbornyl) guanidine hydrochloride White Powder m.p. 144°–145° C.
IR (KBr): 3200, 2950, 2200, 1740 cm$^{-1}$
$^1$H-NMR (DMSO-d$_6$) δ ppm: 10.50 (1H, s), 9.16 (1H, s), 8.17 (1H, d, J=1.4 Hz), 7.74 (2H, m), 7.18 (1H, d, J=6.6 Hz), 4.18 (2H, q, J=7.1 Hz), 3.68 (1H, m), 2.24 (2H, m), 1.72–1.07 (8H, m), 1.26 (3H, t, J=7.1 Hz)

EXAMPLE 47

N-(6-benzyloxycarbonylamino-3-pyridyl)-N''-cyano-N'-(exo-2-norbornyl) quanidine hydrochloride White Powder m.p. 152°–153° C.
IR (KBr): 3200, 2950, 2200, 1720 cm$^{-1}$
$^1$H-NMR (DMSO-d$_6$) δ ppm: 10.76 (1H, s), 9.29 (1H, s), 8.21 (1H, d, J=2.5 Hz), 7.82–7.71 (2H, m), 7.43 (5H, m), 7.27 (1H, d, J=6.7 Hz), 5.21 (2H, s), 3.70 (1H, m), 2.23 (2H, m), 1.72–1.08 (8H, m)

EXAMPLE 48

N-[6-(hexylureido)-3-pyridyl)-N''-cyano-N'-(exo-2-norbornyl) guanidine

Colorless Needle-like Crystal m.p. 157°-158° C.

IR (KBr): 3400-3100, 2950, 2850, 2118, 1670, 1498 cm$^{-1}$ $^1$H-NMR (DMSO-d$_6$) δ ppm: 9.16 (1H, s), 8.73 (1H, s), 8.04 (1H, br), 8.00 (1H, d, J=2.5 Hz), 7.49 (1H, dd, J=2.5 Hz, 8.9 Hz), 7.33 (1H, d, J=8.9 Hz), 6.75 (1H, d, J=6.6 Hz), 3.61 (1H, brs), 3.17 (2H, q, J=6 3 Hz), 2.22 (2H, br), 1.55-1.70 (1H, m), 1.00-1.55 (15H, m), 0.88 (3H, t, J=6.3 Hz)

EXAMPLE 49

(a)

N-[6-(5-methyl-2-oxo-2H-1,3-dioxole-4-ylmethylamino)-3-pyridyl]-N''-cyano-N'-(exo-2-norbornyl) guanidine IR (KBr): 3250, 2900, 2200, 1800, 1720 cm$^{-1}$ $^1$H-NMR (DMSO-d$_6$) δ ppm: 8.50 (1H, s), 7.83 (1H, d, J=2.3 Hz), 7.25 (1H, dd, J=2.4, 8.7 Hz), 7.04 (1H, t, J=5.7 Hz), 6.51 (1H, d, J=8.7 Hz), 6.52 (1H, s), 4.29 (2H, d, J=5.6 Hz), 3.56 (1H, m), 2.19 (2H, m), 2.15 (3H, s), 1.66-1.04 (8H, m)

(b)

N-[6-(5-methyl-2-oxo-2H-1,3-dioxole-4-ylmethylamino)-3-pyridyl]-N'' -cyano-N'-(exo-2-norbornyl) quanidine hydrochloride Light Yellow Powder m p. 151°-152° C. IR (KBr): 3200, 2900, 2150, 1800, 1730 cm$^{-1}$ $^1$H-NMR (DMSO-d$_6$) δ ppm: 9.07 (1H, s), 8.60 (1H, s), 7.94 (1H, d, J=2.2 Hz), 7.78 (1H, dd, J=2.0, 9.3 Hz), 7.12 (1H, d, J=6.5 Hz), 7.00 (1H, d, J=9.3 Hz), 4.53 (2H, s), 3.65 (1H, m), 2.23 (2H, m), 2.19 (3H, s), 1.71-1.06 (8H, m)

EXAMPLE 50

6-(2-oxopropylamino)-3-pyridyl]-N''-cyano-N'-(exo-2-norbornyl) guanidine

Light Yellow Powder m.p. 117°-119° C.

IR (KBr): 3500, 3350, 3200, 3000, 2950, 2150, 1720, 1590, 1610 cm$^{-1}$ $^1$H-NMR (CDCl$_3$) δ ppm: 7.94 (1H, d, J=2.0 Hz), 7.25 (1H, dd, J=2.0, 10.0 Hz), 7.16 (1H, brs), 6.54 (1H, d, J=10.0 Hz), 5.50 (1H, t, J=7.0 Hz), 4.46 (1H, d, J=3.0 Hz), 4.29 (2H, d, J=7.0 Hz), 3.55-3.7 (1H, m), 2.27 (3H, s), 2.15-2.25 (2H, m), 1.0-1.9 (8H, m)

EXAMPLE 51

(a)

N-(6-methanesulfonylamino-3-pyridyl)-N'-(1,2,2-trimethylpropyl)carbodiimide

N-(6-amino-3-pyridyl)-N'-1,2,2-trimethylpropylthiourea (1.26 g, 5.29 mmol) obtained in Example 21 was dissolved in 10 ml of THF in an atmosphere of nitrogen and 7.38 ml of triethylamine and methanesulfonylchloride (0.41 ml, 5.29 mmol) were successively added dropwise thereto under ice cooling. After completion of the dropping, the mixture was stirred at room temperature for 1.5 hour, followed by addition of water. Extraction with chloroform was repeated three times, the extract was dried and the solvent was removed by distillation. The residue was purified by silica gel column chromatography [eluent: chloroform:methanol =100:1 to 10:1 (v/v)] and subjected to recrystallization from chloroform-ether to obtain 210 mg of the intended product (yield: 13%).

White Crystal

IR (KBr): 3600-3100, 3000, 2950, 2850, 2100 cm$^{-1}$ $^1$H-NMR (DMSO-d$_6$) δ ppm: 8.04 (1H, d, J=2.0 Hz), 7.47 (1H, dd, J=2.0, 8.0 Hz), 6.95 (1H, d, J=8.0 Hz), 3.54 (1H, q, J=6.0 Hz), 3.27 (3H, s), 1.25 (3H, d, J=6.0 Hz), 0.92 (9H, s)

$^{13}$C-NMR (DMSO-d$_6$) δ ppm: 154.8, 145.8, 137.2, 133.0, 128.3, 113.1, 52.6, 41.5, 34.1, 26.1, 16.4

(b)

N-(6-methanesulfonylamino-3-pyridyl)-N'''-cyano-N'-(1,2,2-trimethylpropyl) guanidine Cyanamide (172 mg, 4.1 mmol) and diisopropylethylamine (711 μl, 4.1 mmol) were added to 1 ml of a solution of N-(6-methanesulfonylamino-3-pyridyl)-N'-(1,2,2-trimethylpropyl)carbodiimide (121 mg, 0.41 mmol) in chloroform and the mixture was stirred at room temperature for 16 hours. After an insoluble matter was removed by filtration, the filtrate was concentrated. The residue was purified by silica gel column chromatography [eluent: chloroform alone to chloroform:methanol =5:1 (v/v)] and subjected to recrystallization from chloroform-ether to obtain 97 mg of the intended product (yield: 72%).

White Crystal m.p. 164°-166° C.

IR (KBr): 3600-3000, 2990, 2290, 2200 cm$^{-1}$ $^1$H-NMR (DMSO-d$_6$) δ ppm: 8.94 (1H, s), 8.11 (1H, d, J=2.0 Hz), 7.58 (1H, dd, J=2.0, 7.0 Hz), 6.95 (1H, d, J=7.0 Hz), 6.73 (1H, d, J=8.0 Hz), 3.7-3.95 (1H, m), 3.27 (3H, s), 1.06 (3H, d, J=6.0 Hz), 0.88 (9H, s)

EXAMPLE 52

N-(6-methylthio-3-pyridyl)-N'-(1,2,2-trimethylpropyl)-thiourea

Using methanethiol in place of methylamine, the above-described compound was synthesized in accordance with the method described in Example 28.

White Powder m.p. 157.0°-158.0° C.

IR (KBr): 3220, 2950, 1530, 1465, 1140 cm$^{-1}$ $^1$H-NMR (CDCl$_3$) δ ppm: 8.36 (1H, d, J=2.5 Hz), 7.83 (1H, brs), 7.41 (1H, dd, J=8.7, 2.5 Hz), 7.25 (1H, dd, J=8.7, 0.5 Hz), 5.60-5.85 (1H, brd), 4.25-4.55 (1H, m), 2.58 (3H, s), 1.11 (3H, d, J=6.7 Hz), 0.89 (9H, s)

EXAMPLES 53 To 83

The compounds shown in Table 4 were synthesized in accordance with the methods described in Examples 1-8 or 21. The properties of the obtained compounds were shown in Table 4 in which the symbol "*" at the column of the compound (R) indicates the binding position.

TABLE 4

Structure: H2N-pyridine-NH-C(=Z)-NH-R

| Example No. | Compound (R) | m.p. (°C.) | Appearance | Specific rotation $[\alpha]_D$ (temperature, solvent) |
|---|---|---|---|---|
| (A) Z=S | | | | |
| 53 | 2-methylcyclohexyl (chiral) | 178–180 | red brown crystal | $[\alpha]_D^{20} = +16.7$ (c 0.2, MeOH) |
| 54 | bicyclic | 174–180 | light pink crystal | |
| 55 (Hydrochloride) | cyclohexenyl | unmeasurable | light brown amorphous | |
| 56 | 2-methylcyclohexyl | 174–175.5 | light pink crystal | |
| 57 | cyclohexyl | 173–174 | light pink crystal | |
| 58 | cyclohexyl | 138–140 | white crystal | |
| 59 | adamantyl | 165–167 | light needle-like crystal | |
| 60 | 2,6-dimethylcyclohexyl | 112–114 | gray crystal | $[\alpha]_D^{22} = +15.5$ (c 0.2, MeOH) |
| 61 | 4,4-dimethylcyclohexyl | 152–154.5 | light brown crystal | |
| 62 | hydrindanyl | 153–154 | colorless transparent prism crystal | |

TABLE 4-continued

Structure: 2-amino-5-(NH-C(=Z)-NH-R)-pyridine

| Example No. | Compound (R) | m.p. (°C.) | Appearance | Specific rotation $[\alpha]_D$ (temperature, solvent) |
|---|---|---|---|---|
| 63 | (1-methylcyclohex-2-enyl) | 188–189 | red brown crystal | |
| 64 | (cyclohex-2-enylmethyl) | 178–180 | brown crystal | $[\alpha]_D^{22} = -2.7$ (c 0.3, MeOH) |
| 65 (Hydrochloride) | (pinanyl) | 190 (Decomposition) | brown crystal | $[\alpha]_D^{22} = +7.0$ (c 0.2, MeOH) |
| 66 (Hydrochloride) | (cyclohexylmethyl) | 153–154 | light brown powder | |
| 67 | (2-cyclohexylprop-2-yl / isopropylcyclohexyl) | 182–184 | red brown crystal | |
| 68 (Hydrochloride) | (4-methylcyclohex-2-enyl) | 206–207 | dark brown crystal | |
| 69 | (2,2-dimethylcyclopentyl) | 187–188 | gray brown crystal | |
| 70 | (trans-dimethylcyclopentyl) | 171–172 | pink needle-like crystal | |
| 71 | (cis-cyclohexyl disubstituted) | 142–143 | light brown plate-like crystal | |
| 72 | (trans-1,3-cyclohexyl) | 168–169 | colorless plate-like crystal | |

TABLE 4-continued

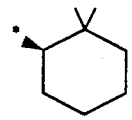

| Example No. | Compound (R) | m.p. (°C.) | Appearance | Specific rotation [α]$_D$ (temperature, solvent) |
|---|---|---|---|---|
| 73 | 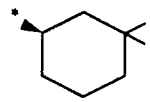 | 90-92 | violet amorphous | |
| 74 | 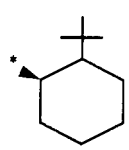 | 109-110 | violet amorphous | |
| 75 | 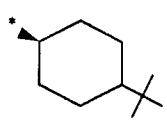 | 166-168 | mauve crystal | |
| 76 (cys form) | 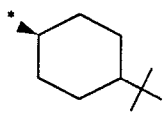 | 176-177.5 | brown needle-like crystal | |
| 77 (trans form) | 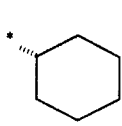 | 194-196 | white powder | |
| (B) Z=NCN | | | | |
| 78 | 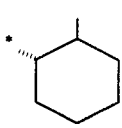 | 183-190 | white needle-like crystal | |
| 79 | 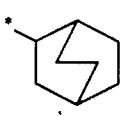 | 189-190 | colorless needle-like crystal | |
| 80 |  | 208.5-210 | white needle-like crystal | |
| 81 (Hydrochloride) |  | 220-225 (Decomposition) | white powder | |
| 82 | —C(CH$_3$)$_3$ | 220-221 | light red crystal | |
| 83 (Hydrochloride) | —C(CH$_3$)$_3$ | 213-217 | white crystal | |

EXAMPLE 84

N-(6-aminopyridine-1-oxido-3-yl)-N''-cyano-N'-(1,2,2-trimethylpropyl) guanidine N-(6-amino-3-pyridyl)-N''-cyano-N'-(1,2,2-trimethylpropyl) guanidine (1.757 g, 6.749 mmol) obtained in Example 25 was dissolved in a mixed solvent of methylene chloride-methanol (4:1 (v/v), 25 ml), m-chloroperbenzoic acid (1.664 g, purity: 70%, 6.749 mmol) was gradually added thereto under ice cooling. The reaction mixture was stirred under ice cooling for 2 hours and 50 mg of sodium sulfite was added thereto followed by stirring for 10 minutes. Then, 30 ml of a 10% potassium carbonate aqueous solution was added to the reaction mixture and subjected to extraction with chloroform. After the extract was dried, the solvent was removed. The residue was purified by silica gel column chromatography (eluent: chloroform:methanol=10:1 (v/v)). Recrystallization from methanol-methylene chloride-ether gave 1.459 g of the intended product (yield 78.2%).

Light Brown Powder m.p. 141.0°–146.0° C.

$^1$H-NMR (DMSO-d$_6$) δ ppm: 8.78 (1H, s), 7.90 (1H, d, J=2.2 Hz), 6.98 (1H, dd, J=8.8, 2.2 Hz), 6.77 (2H, s), 6.77 (1H, d, J=8.8 Hz), 6.61 (1H, d, J=9.2 Hz), 3.65–3.90 (1H, m), 1.01 (3H, d, J=6.8 Hz), 0.85 (9H, s)

EXAMPLE 85

Using N-(6-amino-3-pyridyl)-N''-cyano-N'-(exo-2-norbornyl) guanidine obtained in Example 43 as a starting material, the following compound was obtained in the same manner as Example 84.

N-(6-aminooyridine-1-oxido-3-yl)-N''-cyano-N'-(exo-2-norbornyl)guanidine

White Powder m.p. 156.0°–160.0° C.

$^1$H-NMR (DMSO-d$_6$) δ ppm: 8.66 (1H, s), 7.90 (1H, d, J=2.2 Hz), 6.98 (1H, dd, J=8.9, 2.2 Hz), 6.75 (1H, brs), 6.75 (1H, d, J=8.9 Hz), 6.75 (2H, s), 3.45–3.65 (1H, m), 2.10–2.25 (2H, m), 1.00–1.70 (8H, m)

EXAMPLES 86 To 88

The compounds shown in Table 5 were synthesized in accordance with the method described in Example 84.

TABLE 5

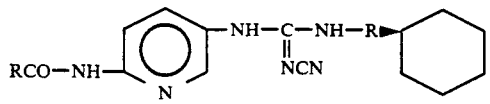

| Example No. | Compound (R) | m.p. (°C.) | Appearance |
|---|---|---|---|
| 86 | 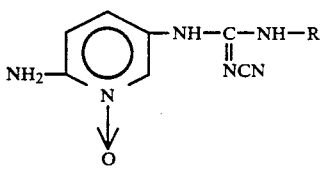 | 231–232 (Decomposition) | milk-white powder |

TABLE 5-continued

| Example No. | Compound (R) | m.p. (°C.) | Appearance |
|---|---|---|---|
| 87 | 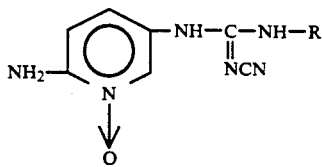 | 155–161 (Decomposition) | light yellow linear crystal |
| 88 | —C(CH$_3$)$_3$ | 231–232 | white powder |

EXAMPLES 89 To 92

The compounds shown in Table 6 were synthesized in accordance with the method described in Example 45.

TABLE 6

| Example No. | Compound (R) | m.p. (°C.) | Property |
|---|---|---|---|
| 89 | NH$_2$CH$_2$— | 210–211 (Decomposition) | colorless plate-like crystal |
| 90 | H-N (pyrrolidinyl) | 123–126 | |
| 91 | (CH$_3$)$_2$CHCH(NH$_2$)— | 114–116 | |
| 92 | CH$_3$SCH$_2$CH$_2$CH(NH$_2$)— | unmeasurable (Hygroscopic) | light yellow solid |

EXAMPLE 93

6-Amino-3-(2-endo-norbornylamino-2-nitroethenylamino)pyridine

The above-described compound can be synthesized in accordance with the method described in Example 23 except for using 2,5-diaminopyridine in place of 3,4-diaminopyridine.

PHARMACOLOGICAL TESTS

In order to show the utility of the compounds of the present invention, results of pharmacological tests for typical compounds are shown below.

(A) Vasodepressor Activity (1) Test method

Male Wistar rats having a body weight of 300 g were used for the test. The rat intravenously anesthetized with 50 mg/kg of pentobarbital sodium was fixed at its back, and a polyethylene catheter was inserted into the left common carotid artery for measurement of the blood pressure. The blood pressure and the heart rate were continuously recorded on a polygraph through a tachometer and a pressure transducer. The drug was given in bolus form through a wing-like needle placed in the caudal vein.

(2) Test results

Test results are shown in Table 2.

TABLE 2

| Test Compound (Example No.) | Dosage (mg/kg) | Maximum Effect (%) | |
|---|---|---|---|
| | | Diastolic Pressure | Systolic Pressure |
| 7 | 3 | 73 | 59 |
| 24 | 3 | 71 | 52 | note: Maximum effect indicates the parcentage of the lowest blood pressure after administration of the drug based on the blood pressure before the administration of the drug.

(B) Activity on Autonomous Contraction of Portal Vein Extirpated from Rat (1) Test method A male Wistar rat having a body weight of 300 g was slaughtered by striking a blow at the occipital region, and the portal vein was extirpated therefrom. The extirpated vein was cut longitudinally to prepare strip section samples about 1 cm in length. The portal vein samples to which a load of 0.5 g was applied were suspended in Locke solution aerated with a mixed gas (95% $O_2$ and 5% $CO_2$) in a Magnus bath at 37° C., and changes in contraction tension were recorded on a thermal stylus recorder through a transducer.

The portal vein samples were thus allowed to conduct a rhythmic movement for about 30 minutes. When the rhythm was stabilized, the drug was accumulatively added. To the samples in which the automatic rhythm of the portal vein disappeared by addition of the drug, glibenclamide as a potassium channel blocker, was added at a concentration of $10^{-6}$ to $10^{-5}$ M, or 3,4-diaminopyridine at a concentration of $10^{-4}$ to $10^{-3}$ M, whereby the recovery of the automatic rhythm was examined.

(2) Test results

Test results are shown in Table 3.

TABLE 3

| Test Compound (Example No.) | $IC_{100}$ (μM) |
|---|---|
| 7 | 10 |
| 24 | 1 |

For the test compounds, the autonomous contraction of the rat portal vein was allowed to disappear at the $IC_{100}$ concentrations shown in Table 3. The autonomous contraction was recovered by adding glibenclamide at $10^{-6}$ M or 3,4-diaminopyridine at $10^{-3}$ M.

While the invention has been described in detail and with reference to specific examples thereof, it will be apparent to one skilled in the art that various changes and modifications can be made therein without departing from the spirit and scope thereof.

What is claimed is:

1. An aminopyridine compound represented by the formula:

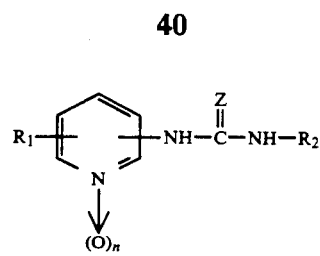

wherein n represents 0 to 1; Z represents =S, =NCN or =CHNO$_2$; R$_1$ represents —NR$_3$R$_4$, —NHNR$_3$R$_4$, —NHCONHR$_3$ or —NHSO$_2$R$_3$; R$_2$ represents H, substituted or unsubstituted alkyl, or substituted or unsubstituted cycloalkyl; R$_3$ and R$_4$, which may be the same or different, represent H, substituted or unsubstituted alkyl, substituted or unsubstituted cycloalkyl, substituted or unsubstituted aryl, substituted or unsubstituted alphatic acyl or aromatic acyl, or alkoxycarbonyl group; and R$_3$ and R$_4$ may form a substituted or unsubstituted heterocyclic ring together with the nitrogen atom to which R$_3$ and R$_4$ are bound, which ring may include another heteroatom and may contain unsaturation;

wherein each alkyl group has from 1 to 10 carbon atoms, each cycloalkyl group has from 5 to 10 carbon atoms, the aryl is selected from the group consisting of phenyl and naphthyl, the aliphatic acyl is selected from the group consisting of acetyl, propionyl, butyryl, isobutyryl, valeryl, and pivaloyl, the aromatic acyl is selected from the group consisting of benzoyl, naphthoyl and toluoyl, and the alkoxycarbonyl has an alkoxy portion having from 1 to 7 carbon atoms, wherein each substituted alkyl contains a substituent selected from the group consisting of hydroxyl and amino, each substituted cycloalkyl contains an alkyl substituent, the substituted aryl contains a substituent selected from the group consisting of alkyl, halogen, nitro, and cyano, and the substituted acyl contains a substituent selected from the group consisting of amino, lower alkoxycarbonylamino, carboxy, and a heterocyclic ring, wherein each heterocyclic ring is selected from the group consisting of pyrrolidinyl, piperidino, pyrrolinyl, pyrrolyl, piperazinyl, morpholino, thiomorpholino, imidazolinyl, imidizolidinyl, imidazolyl and pyrazolidinyl, wherein the substituted heterocyclic ring contains a substituent selected from the group consisting of alkyl, acyl, aryl and alkoxycarbonyl as defined above;

or a pharmaceutically acceptable acid salt thereof.

2. The compound of claim 1, wherein each alkyl group is straight or branched chain.

3. The compound of claim 2, wherein each alkyl group is straight or branched chain containing 1 to 10 carbon atoms.

4. The compound of claim 1, wherein each cyclo alkyl group is a monocycloallyl group containing 5 to 7 carbon atoms.

5. The compound of claim 1, wherein each cyclo alkyl group is a bicycloalkyl group containing 7 to 10 carbon atoms.

6. The compound of claim 1, wherein the acyl group is an aliphatic acyl group.

7. The compound of claim 1, wherein the acyl group is an aromatic acyl group.

8. The compound of claim 1, wherein the alkoxy component in the alkoxycarbonyl group has from 1 to 4 carbon atoms.

9. The compound of claim 1, wherein when $R_3$ and $R_4$ combine with the nitrogen to form a heterocyclic ring, $R_3$ and $R_4$ are independently alkylene or alkenylene, wherein the alkylene is selected from the group consisting of methylene, ethylene, trimethylene, propylene, tetramethylene, and 1,2-dimethylethylene, and the alkenylene is selected from the group consisting of 1-butenylene and 1,3-butadienylene.

10. The compound of claim 8, wherein the heterocyclic ring formed is imidazolyl of

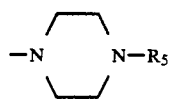

in which $R_5$ is H, alkyl, acyl, aryl or alkoxycarbonyl.

11. The compound of claim 1, wherein $R_1$ is bound at the 4-position of the pyridine ring.

12. The compound of claim 1, wherein $R_1$ is bound at the 6-position of the pyridine ring.

13. The compound of claim 1, wherein the group $-NH-C(=Z)-NHR_2$ is bound at the 3-position of the pyridine ring.

14. The compound of claim 1, wherein Z is =S.

15. The compound of claim 1, wherein Z is =NCN.

16. The compound of claim 1, wherein Z is —CH-NO$_2$.

17. A process for treating hypertension which comprises administering to a patient in need of treatment for hypertension, a hypertension reducing effective amount of a compound of claim 1.

18. A process for treating ischemic heart disease which comprises administering to a patient in need of treatment for ischemic heart disease an ischemic heart disease treating effective amount of a compound of claim 1.

19. A process for vasodilating the peripheral, coronary or cerebral blood vessels which comprises administering, to a patient in need of vasodilation, an amount of a compound of claim 1 effective to dilate the peripheral, coronary or cerbral blood vessels.

20. A process for treating lipodysbolism which comprises administering to a patient in need of treatment for lipodysbolism, a lipodysbolism treating effective amount of a compound of claim 1.

* * * * *